(12) United States Patent
Juhasz et al.

(10) Patent No.: US 8,459,794 B2
(45) Date of Patent: Jun. 11, 2013

(54) IMAGE-PROCESSOR-CONTROLLED MISALIGNMENT-REDUCTION FOR OPHTHALMIC SYSTEMS

(75) Inventors: Tibor Juhasz, Corona del Mar, CA (US); Ferenc Raksi, Mission Viejo, CA (US); Guy Holland, San Clemente, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 259 days.

(21) Appl. No.: 13/098,586

(22) Filed: May 2, 2011

(65) Prior Publication Data

US 2012/0281185 A1 Nov. 8, 2012

(51) Int. Cl.
*A61B 3/10* (2006.01)

(52) U.S. Cl.
USPC .............................. 351/208; 351/204; 351/246

(58) Field of Classification Search
USPC ................... 351/204, 246, 200, 208; 606/4, 5
See application file for complete search history.

(56) References Cited

U.S. PATENT DOCUMENTS

| | | | |
|---|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A | 8/1985 | Ishikawa |
| 4,538,608 A | 9/1985 | L'Esperance, Jr. |
| 4,554,917 A | 11/1985 | Tagnon |
| 4,638,801 A | 1/1987 | Daly et al. |
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,112,328 A | 5/1992 | Taboada et al. |
| 5,139,022 A | 8/1992 | Lempert |
| 5,246,435 A | 9/1993 | Bille et al. |

(Continued)

FOREIGN PATENT DOCUMENTS

| EP | 1444946 | 8/2004 |
|---|---|---|
| EP | 2322083 | 5/2011 |

(Continued)

OTHER PUBLICATIONS

Arimoto et al., "Imaging Properties of Axicon in a Scanning Optical System," Nov. 1, 1992, Applied Optics, 31 (31):6652-6657.

(Continued)

*Primary Examiner* — Hung Dang

(57) ABSTRACT

An ophthalmic system is provided that includes an ophthalmic imaging device to generate an image of a portion of an imaged eye of a patient, an image processor to determine a misalignment of the imaged eye and the imaging device by processing the generated image, and to generate a control signal according to the determined misalignment, and a misalignment-reduction system to receive the control signal, and to generate a misalignment-reduction response. The misalignment-reduction system can include a fixation light system or a gantry. In some cases a locator light system may provide additional alignment information for the image processor.

46 Claims, 27 Drawing Sheets

U.S. PATENT DOCUMENTS

| | | | |
|---|---|---|---|
| 5,255,025 A | 10/1993 | Volk | |
| 5,286,964 A | 2/1994 | Fountain | |
| 5,321,501 A | 6/1994 | Swanson et al. | |
| 5,336,215 A | 8/1994 | Hsueh et al. | |
| 5,391,165 A | 2/1995 | Fountain et al. | |
| 5,439,462 A | 8/1995 | Bille et al. | |
| 5,493,109 A | 2/1996 | Wei et al. | |
| 5,549,632 A | 8/1996 | Lai | |
| 5,656,186 A | 8/1997 | Mouron et al. | |
| 5,738,676 A | 4/1998 | Hammer et al. | |
| 5,779,696 A | 7/1998 | Berry et al. | |
| 5,795,295 A | 8/1998 | Hellmuth et al. | |
| 5,936,706 A | 8/1999 | Takagi | |
| 5,954,648 A | 9/1999 | Van Der Brug | |
| 5,954,711 A | 9/1999 | Ozaki et al. | |
| 5,994,690 A | 11/1999 | Kulkarni et al. | |
| 6,004,314 A | 12/1999 | Wei et al. | |
| 6,095,648 A | 8/2000 | Birngruber et al. | |
| 6,099,522 A | 8/2000 | Knopp et al. | |
| 6,137,585 A | 10/2000 | Hitzenberger et al. | |
| 6,254,595 B1 | 7/2001 | Juhasz et al. | |
| 6,288,784 B1 | 9/2001 | Hitzenberger et al. | |
| 6,314,311 B1 | 11/2001 | Williams et al. | |
| 6,317,616 B1 | 11/2001 | Glossop | |
| 6,337,925 B1 | 1/2002 | Cohen et al. | |
| 6,377,349 B1 | 4/2002 | Fercher | |
| 6,379,005 B1 | 4/2002 | Williams et al. | |
| 6,451,009 B1 | 9/2002 | Dasilva et al. | |
| 6,454,761 B1 | 9/2002 | Freedman | |
| 6,497,701 B2 | 12/2002 | Shimmick et al. | |
| 6,529,758 B2 | 3/2003 | Shahidi | |
| 6,579,282 B2 | 6/2003 | Bille et al. | |
| 6,623,476 B2 | 9/2003 | Juhasz et al. | |
| 6,687,010 B1 | 2/2004 | Horii et al. | |
| 6,730,074 B2 | 5/2004 | Bille et al. | |
| 6,741,359 B2 | 5/2004 | Wei et al. | |
| 6,751,033 B2 | 6/2004 | Goldstein et al. | |
| 6,755,819 B1 | 6/2004 | Waelti | |
| 6,763,259 B1 | 7/2004 | Hauger et al. | |
| 6,769,769 B2 | 8/2004 | Podoleanu et al. | |
| 6,775,007 B2 | 8/2004 | Izatt et al. | |
| 6,863,667 B2 | 3/2005 | Webb et al. | |
| 6,887,232 B2 | 5/2005 | Bille | |
| 6,899,707 B2 | 5/2005 | Scholler et al. | |
| 6,932,807 B1 | 8/2005 | Tomita et al. | |
| 6,991,629 B1 | 1/2006 | Juhasz et al. | |
| 7,006,232 B2 | 2/2006 | Rollins et al. | |
| 7,018,376 B2 | 3/2006 | Webb et al. | |
| 7,027,233 B2 | 4/2006 | Goldstein et al. | |
| 7,061,622 B2 | 6/2006 | Rollins et al. | |
| 7,072,045 B2 | 7/2006 | Chen et al. | |
| 7,072,047 B2 | 7/2006 | Westphal et al. | |
| 7,079,254 B2 | 7/2006 | Kane et al. | |
| 7,102,756 B2 | 9/2006 | Izatt et al. | |
| 7,113,818 B2 | 9/2006 | Podoleanu et al. | |
| 7,126,693 B2 | 10/2006 | Everett et al. | |
| 7,130,054 B2 | 10/2006 | Ostrovsky et al. | |
| 7,133,137 B2 | 11/2006 | Shimmick | |
| 7,139,077 B2 | 11/2006 | Podoleanu et al. | |
| 7,145,661 B2 | 12/2006 | Hitzenberger | |
| 7,148,970 B2 | 12/2006 | de Boer | |
| 7,184,148 B2 | 2/2007 | Alphonse | |
| 7,207,983 B2 | 4/2007 | Hahn et al. | |
| 7,248,371 B2 | 7/2007 | Chan et al. | |
| 7,268,885 B2 | 9/2007 | Chan et al. | |
| 7,280,221 B2 | 10/2007 | Wei | |
| 7,307,733 B2 | 12/2007 | Chan et al. | |
| 7,310,150 B2 | 12/2007 | Guillermo et al. | |
| 7,312,876 B2 | 12/2007 | Chan et al. | |
| 7,319,566 B2 | 1/2008 | Prince et al. | |
| 7,329,002 B2 | 2/2008 | Nakanishi | |
| 7,330,270 B2 | 2/2008 | O'Hara et al. | |
| 7,330,273 B2 | 2/2008 | Podoleanu et al. | |
| 7,335,223 B2 | 2/2008 | Obrebski | |
| 7,336,366 B2 | 2/2008 | Choma et al. | |
| 7,342,659 B2 | 3/2008 | Horn et al. | |
| 7,347,548 B2 | 3/2008 | Huang et al. | |
| 7,352,444 B1 | 4/2008 | Seams et al. | |
| 7,355,716 B2 | 4/2008 | de Boer et al. | |
| 7,364,296 B2 | 4/2008 | Miller et al. | |
| 7,365,856 B2 | 4/2008 | Everett et al. | |
| 7,365,859 B2 | 4/2008 | Yun et al. | |
| 7,370,966 B2 | 5/2008 | Fukuma et al. | |
| 7,371,230 B2 | 5/2008 | Webb et al. | |
| 7,372,578 B2 | 5/2008 | Akiba et al. | |
| 7,388,672 B2 | 6/2008 | Zhou et al. | |
| 7,390,089 B2 | 6/2008 | Loesel et al. | |
| 7,400,410 B2 | 7/2008 | Baker et al. | |
| 7,402,159 B2 | 7/2008 | Loesel et al. | |
| 7,426,037 B2 | 9/2008 | Ostrovsky et al. | |
| 7,433,046 B2 | 10/2008 | Everett et al. | |
| 7,452,077 B2 | 11/2008 | Meyer et al. | |
| 7,452,080 B2 | 11/2008 | Wiltberger et al. | |
| 7,461,658 B2 | 12/2008 | Jones et al. | |
| 7,466,423 B2 | 12/2008 | Podoleanu et al. | |
| 7,470,025 B2 | 12/2008 | Iwanaga | |
| 7,477,764 B2 | 1/2009 | Haisch | |
| 7,480,058 B2 | 1/2009 | Zhao et al. | |
| 7,480,059 B2 | 1/2009 | Zhou et al. | |
| 7,488,070 B2 | 2/2009 | Hauger et al. | |
| 7,488,930 B2 | 2/2009 | Ajgaonkar et al. | |
| 7,492,466 B2 | 2/2009 | Chan et al. | |
| 7,503,916 B2 | 3/2009 | Shimmick | |
| 7,508,525 B2 | 3/2009 | Zhou et al. | |
| 7,535,577 B2 | 5/2009 | Podoleanu et al. | |
| 7,537,591 B2 | 5/2009 | Feige et al. | |
| 7,557,928 B2 | 7/2009 | Ueno | |
| 7,575,322 B2 | 8/2009 | Somani | |
| 7,593,559 B2 | 9/2009 | Toth et al. | |
| 7,602,500 B2 | 10/2009 | Izatt et al. | |
| 7,604,351 B2 | 10/2009 | Fukuma et al. | |
| 7,614,744 B2 | 11/2009 | Abe | |
| 7,630,083 B2 | 12/2009 | de Boer et al. | |
| 7,631,970 B2 | 12/2009 | Wei | |
| 7,633,627 B2 | 12/2009 | Choma et al. | |
| 7,643,152 B2 | 1/2010 | de Boer et al. | |
| 7,797,119 B2 | 9/2010 | De Boer et al. | |
| 7,813,644 B2 | 10/2010 | Chen et al. | |
| 7,898,712 B2 | 3/2011 | Adams et al. | |
| 8,262,646 B2 | 9/2012 | Frey et al. | |
| 8,394,084 B2 | 3/2013 | Palankar et al. | |
| 2001/0022648 A1 | 9/2001 | Lai | |
| 2002/0013574 A1 | 1/2002 | Elbrecht et al. | |
| 2002/0082466 A1 | 6/2002 | Han | |
| 2002/0097374 A1 | 7/2002 | Payne et al. | |
| 2002/0133145 A1 | 9/2002 | Gerlach et al. | |
| 2002/0198516 A1 | 12/2002 | Knopp | |
| 2003/0090674 A1 | 5/2003 | Zeylikovich et al. | |
| 2003/0206272 A1 | 11/2003 | Cornsweet et al. | |
| 2004/0039378 A1 | 2/2004 | Lin | |
| 2004/0059321 A1 | 3/2004 | Knopp et al. | |
| 2004/0151466 A1 | 8/2004 | Crossman-Bosworth et al. | |
| 2004/0243233 A1 | 12/2004 | Phillips | |
| 2005/0010109 A1 | 1/2005 | Faul | |
| 2005/0015120 A1 | 1/2005 | Seibel et al. | |
| 2005/0021011 A1 | 1/2005 | LaHaye | |
| 2005/0173817 A1 | 8/2005 | Fauver et al. | |
| 2005/0192562 A1 | 9/2005 | Loesel et al. | |
| 2005/0201633 A1 | 9/2005 | Moon et al. | |
| 2005/0203492 A1 | 9/2005 | Nguyen et al. | |
| 2005/0215986 A1 | 9/2005 | Chernyak et al. | |
| 2005/0284774 A1 | 12/2005 | Mordaunt | |
| 2005/0286019 A1 | 12/2005 | Wiltberger et al. | |
| 2005/0288745 A1 | 12/2005 | Andersen et al. | |
| 2006/0020172 A1 | 1/2006 | Luerssen et al. | |
| 2006/0077346 A1 | 4/2006 | Matsumoto | |
| 2006/0100613 A1 | 5/2006 | McArdle et al. | |
| 2006/0179992 A1 | 8/2006 | Kermani | |
| 2006/0187462 A1 | 8/2006 | Srinivasan et al. | |
| 2006/0195076 A1 | 8/2006 | Blumenkranz et al. | |
| 2006/0206102 A1 | 9/2006 | Shimmick | |
| 2007/0013867 A1 | 1/2007 | Ichikawa | |
| 2007/0121069 A1 | 5/2007 | Andersen et al. | |
| 2007/0126985 A1 | 6/2007 | Wiltberger et al. | |
| 2007/0129709 A1 | 6/2007 | Andersen et al. | |
| 2007/0129775 A1 | 6/2007 | Mordaunt et al. | |
| 2007/0147730 A1 | 6/2007 | Wiltberger et al. | |

| | | | |
|---|---|---|---|
| 2007/0173791 | A1 | 7/2007 | Raksi |
| 2007/0173794 | A1 | 7/2007 | Frey et al. |
| 2007/0173795 | A1 | 7/2007 | Frey et al. |
| 2007/0185475 | A1 | 8/2007 | Frey et al. |
| 2007/0189664 | A1 | 8/2007 | Andersen et al. |
| 2007/0216909 | A1 | 9/2007 | Everett et al. |
| 2007/0219541 | A1 | 9/2007 | Kurtz |
| 2007/0230520 | A1 | 10/2007 | Mordaunt et al. |
| 2007/0282313 | A1 | 12/2007 | Huang et al. |
| 2007/0291277 | A1 | 12/2007 | Everett et al. |
| 2007/0299429 | A1 | 12/2007 | Amano |
| 2008/0033406 | A1 | 2/2008 | Andersen et al. |
| 2008/0049188 | A1 | 2/2008 | Wiltberger et al. |
| 2008/0055543 | A1 | 3/2008 | Meyer et al. |
| 2008/0056610 | A1 | 3/2008 | Kanda |
| 2008/0071254 | A1 | 3/2008 | Lummis et al. |
| 2008/0088795 | A1 | 4/2008 | Goldstein et al. |
| 2008/0100612 | A1 | 5/2008 | Dastmalchi et al. |
| 2008/0281303 | A1 | 11/2008 | Culbertson et al. |
| 2008/0281413 | A1 | 11/2008 | Culbertson et al. |
| 2008/0319427 | A1 | 12/2008 | Palanker |
| 2009/0012507 | A1 | 1/2009 | Culbertson et al. |
| 2009/0088734 | A1 | 4/2009 | Mordaunt |
| 2009/0125005 | A1 | 5/2009 | Chernyak et al. |
| 2009/0131921 | A1 | 5/2009 | Kurtz et al. |
| 2009/0149742 | A1 | 6/2009 | Kato et al. |
| 2009/0157062 | A1 | 6/2009 | Hauger et al. |
| 2009/0161827 | A1 | 6/2009 | Gertner et al. |
| 2009/0168017 | A1 | 7/2009 | O'Hara et al. |
| 2009/0177189 | A1 | 7/2009 | Raksi |
| 2009/0268161 | A1 | 10/2009 | Hart et al. |
| 2010/0004641 | A1 | 1/2010 | Frey et al. |
| 2010/0004643 | A1 | 1/2010 | Frey et al. |
| 2010/0007848 | A1 | 1/2010 | Murata |
| 2010/0022994 | A1 | 1/2010 | Frey et al. |
| 2010/0022995 | A1 | 1/2010 | Frey et al. |
| 2010/0022996 | A1 | 1/2010 | Frey et al. |
| 2010/0042079 | A1 | 2/2010 | Frey et al. |
| 2010/0110377 | A1 | 5/2010 | Maloca et al. |
| 2010/0208199 | A1* | 8/2010 | Levis et al. ............... 351/204 |
| 2010/0324543 | A1 | 12/2010 | Kurtz et al. |
| 2011/0022036 | A1 | 1/2011 | Frey et al. |
| 2011/0118609 | A1 | 5/2011 | Goldshleger et al. |
| 2011/0196350 | A1 | 8/2011 | Friedman et al. |
| 2011/0202044 | A1 | 8/2011 | Goldshleger et al. |
| 2011/0222020 | A1 | 9/2011 | Izatt et al. |
| 2011/0319873 | A1 | 12/2011 | Raksi et al. |
| 2012/0274903 | A1 | 11/2012 | Sayeram et al. |

FOREIGN PATENT DOCUMENTS

| | | |
|---|---|---|
| JP | 4-503913 | 7/1992 |
| JP | 2002345758 | 12/2002 |
| JP | 2004-531344 | 10/2004 |
| JP | 2009-523556 | 6/2009 |
| WO | 90/09141 | 8/1990 |
| WO | 98/08048 | 2/1998 |
| WO | 03/002008 | 1/2003 |
| WO | 03/062802 | 7/2003 |
| WO | 2006074469 | 7/2006 |
| WO | 2007/084694 | 7/2007 |
| WO | 2007106326 | 9/2007 |
| WO | 2007/130411 | 11/2007 |
| WO | 2010/075571 | 7/2010 |

OTHER PUBLICATIONS

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27.

Chinn, S.R., et al., "Optical coherence tomography using a frequency-tunable optical source", Optics Letters, 22 (5):340-342, Mar. 1997.

European Search Report, European Patent Application No. 10191057.8, mailed Mar. 16, 2011, to be published by the USPTO.

Fercher et al., "Eye-Length Measurement by Interferometry With Partially Coherent Light," Mar. 1988, Optics Letters, 13(3):186-188.

Fercher et al., "Measurement of Intraocular Distances by Backscattering Spectral Interferometry," May 15, 1995, Optics Comm. 117:43-48.

Hee, M., et al., "Femtosecond transillumination optical coherence tomography", Optics Letters, 18(12):950-952, Jun. 1993.

Huber, R., et al., "Three-dimensional and C-mode OCT imaging with a compact, frequency swept laser source at 1300 nm", Optics Express, 13(26):10523-10538, Dec. 2005.

Izatt et al., "Micron-Resolution Biomedical Imaging With Optical Coherence Tomography," Oct. 1993, Optics & Photonics News, pp. 14-19.

Kamensky, V., et al., "In situ monitoring of the middle IR laser ablation of a cataract-suffered human lens by optical coherent tomography", Proc. SPIE, 2930:222-229, 1996.

Kamensky, V., et al., "Monitoring and animation of laser ablation process in cataracted eye lens using coherence tomography", Proc. SPIE, 2981:94-102, 1997.

Massow, O., et al., "Optical coherence tomography controlled femtosecond laser microsurgery system", Proceedings of the SPIE—Optical Coherence Tomography and Coherence Techniques III, vol. 6627, pp. 662717(1)-662717(6), Aug. 2007.

Ohmi, M., et al., "In-situ Observation of Tissue Laser Ablation Using Optical Coherence Tomography", Optical and Quantum Electronics, 37(13-15):1175-1183, Dec. 2005.

PCT International Search Report for International Application No. PCT/US2011/023710 mailed Aug. 24, 2011.

PCT International Search Report for International Application No. PCT/US2011/025332 mailed Sep. 16, 2011.

PCT International Search Report for International Application No. PCT/US2010/056701 mailed Jan. 12, 2011.

PCT International Search Report for International Application No. PCT/US2008/075511 mailed Mar. 12, 2009.

Sarunic, M., et al., "Instantaneous complex conjugate resolved spectral domain and swept-source OCT using 3×3 fiber couplers", Optics Express, 13(3):957-967, Feb. 2005.

Sarunic, M., et al., "Real-time quadrature projection complex conjugate resolved Fourier domain optical coherence tomography", Optics Letters, 31(16):2426-2428, Aug. 2006.

Sarunic, M., et al., "Imaging the Ocular Anterior Segment With Real-Time, Full-Range Fourier-Domain Optical Coherence Tomography", Archives of Ophthalmology, 126(4):537-542, Apr. 2008.

Stern et al., "Femtosecond Optical Ranging of Corneal Incision Depth," Jan. 1989, Investigative Ophthalmology & Visual Science, 30(1):99-104.

Swanson et al., "In vivo retinal imaging by optical coherence tomography", Optics Letters, 18(21), 1864-1866, Nov. 1993.

Tao, Y., et al., "High-speed complex conjugate resolved retinal spectral domain optical coherence tomography using sinusoidal phase modulation", Optics letters, 32(20):2918-2920, Oct. 2007.

Wojtkowski et al., "In Vivo Human Retinal Imaging by Fourier Domain Optical Coherence Tomography," Jul. 2002, Journal of Biomedical Optics 7(3):457-463, 7 pages.

Yun, S.H., et al., "Wavelength-swept fiber laser with frequency shifted feedback and resonantly swept intra-cavity acoustooptic tunable filter", IEEE Journal of Selected Topics in Quantum Electronics, 3(4):1087-1096, Aug. 1997.

PCT International Search Report corresponding to PCT Application Serial No. PCT/US2011/051466 dated Apr. 10, 2012.

Partial International Search Report corresponding to PCT Application Serial No. PCT/US2012/035927 dated Aug. 3, 2012.

PCT International Search Report dated Dec. 7, 2012 for International Application No. PCT/US2012/035927, filed May 1, 2012.

PCT International Search Report and Written Opinion dated Feb. 9, 2012 for International Application Serial No. PCT/US2011/040223.

Aslyo-Vogel et al., "Darstellung von LTK-Lasionen durch optische Kurzkohärenztomographie (OCT) and Polarisationsmikroskopie nach Sirius-Rot-Fäbung", Ophthalmologe, pp. 487-491, 7-97.

Bagayev et al., "Optical coherence tomography for in situ monitoring of laser corneal ablation", Journal of Biomedical Optics, 7(4), pp. 633-642 (Oct. 2002).

Blaha et al., "The slit lamp and the laser in ophthalmology — a new laser slit lamp", SPIE Optical Instrumentation for Biomedical Laser Applications, vol. 658, pp. 38-42, 1986.

Boppart, S., et al., "Intraoperative Assessment of Microsurgery with Three-dimensional Optical Coherence Tomography", Radiology, 208(1):81-86, Jul. 1998.

Davidson, "Analytic Waveguide Solutions and the Coherence Probe Microscope", Microelectronic Engineering, 13, pp. 523-526, 1991.

Drexler, W., et al., "Measurement of the thickness of fundus layers by partial coherence tomography", Optical Engineering, 34(3):701-710, Mar. 1995.

Dyer, P., et al., "Optical Fibre Delivery and Tissue Ablation Studies using a Pulsed Hydrogen Fluoride Laser", Lasers in Medical Science, 7:331-340, 1992.

Fercher et al., "In Vivo Optical Coherence Tomography", American Journal of Ophthalmology, 116(1), pp. 113-114, 1993.

Fujimoto, J., et al., :Biomedical Imaging using Optical Coherent Tomography, 1994, 67.

Hammer, D., "Ultrashort pulse laser induced bubble creation thresholds in ocular media", SPIE, 2391:30-40, 1995.

Hauger, C., et al., "High speed low coherence interferometer for optical coherence tomography", Proceedings of SPIE, 4619:1-9, 2002.

Hee, M., et al., "Optical Coherence tomography of the Human Retina", Arch Ophthalmol, 113:325-332; Mar. 1995.

Hitzenberger et al., "Interferometric Measurement of Corneal Thickness With Micrometer Precision", American Journal of Ophthalmology, 118:468-476, Oct. 1994.

Hitzenberger, C., et al., "Retinal layers located with a precision of 5 μm by partial coherence interferometry", SPIE, 2393:176-181, 1995.

Itoh et al., "Absolute measurements of 3-D shape using white-light interferometer", SPIE Interferometry: Techniques and Analysis, 1755:24-28, 1992.

Izatt et al., "Ophthalmic Diagnostics using Optical Coherence Tomography", SPIE Ophthalmic Technologies, 1877:136-144, 1993.

Izatt, J., et al., "Micrometer-Scale Resolution Imaging of the Anterior Eye in vivo With Optical Coherence Tomography", Arch Ophthalmol, 112:1584-1589, Dec. 1994.

Jean, B., et al., "Topography assisted photoablation", SPIE, vol. 3591:202-208, 1999.

Kamensky, V., et al., "In Situ Monitoring of Laser Modification Process in Human Cataractous Lens and Porcine Cornea Using Coherence Tomography", Journal of biomedical Optics, 4(1), 137-143, Jan 1999.

Lee et al., "Profilometry with a coherence scanning microscope", Applied Optics, 29(26), 3784-3788, Sep. 10, 1990.

Lubatschowski, "The German Ministry of Research and education funded this OCT guided fs laser surgery in Sep. 2005", http://www.laser-zentrum-hannoverde/download/pdf/taetigkeitsbericht2005.pdf.

Massow, O., et al., "Femtosecond laser microsurgery system controlled by OCT", Laser Zentrum Hannover e.V., The German Ministry of education and research, 19 slides, 2007.

Puliafito, Carmen, "Final technical Report: Air Force Grant #F49620-93-I-03337(1)" dated Feb. 12, 1997, 9 pages.

Ren, Q., et al., "Axicon: A New Laser Beam Delivery System for Corneal Surgery", IEEE Journal of Quantum Electronics, 26(12):2305-2308, Dec. 1990.

Ren, Q., et al., "Cataract Surgery with a Mid-Infrared Endo-laser System", SPIE Ophthalmic Technologies II, 1644:188-192, 1992.

Thompson, K., et al., "Therapeutic and Diagnostic Application of Lasers in Ophthalmology", Proceedings of the IEEE, 80(6):838-860, Jun. 1992.

Thrane, L., et al., "Calculation of the maximum obtainable probing depth of optical coherence tomography in tissue", Proceedings of SPIE, 3915:2-11, 2000.

Wisweh, H., et al., "OCT controlled vocal fold femtosecond laser microsurgery", Laser Zentrum Hannover e.V., The German Ministry of education and research, Grants: 13N8710 and 13N8712; 23 slides, 2008.

\* cited by examiner

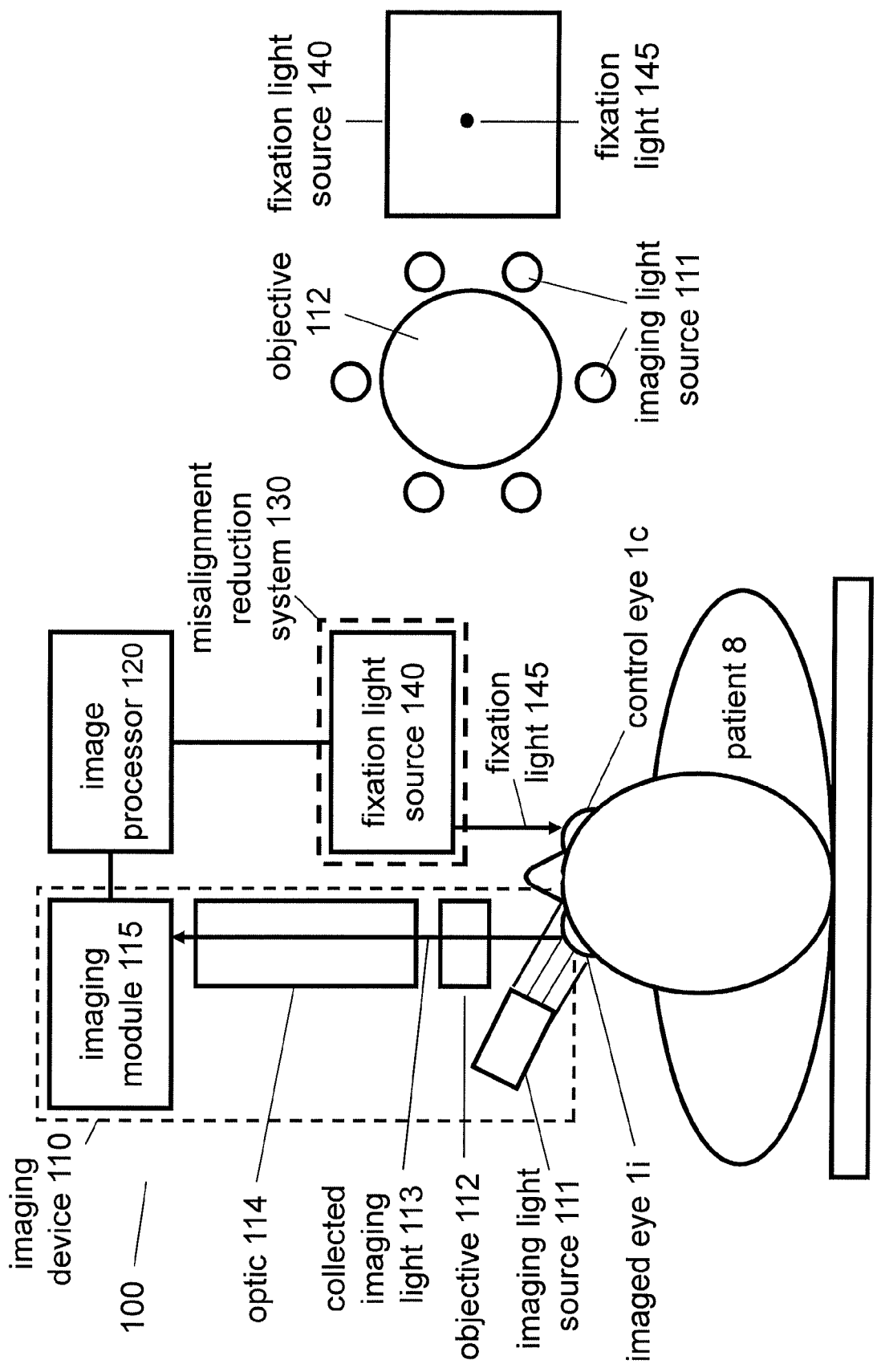

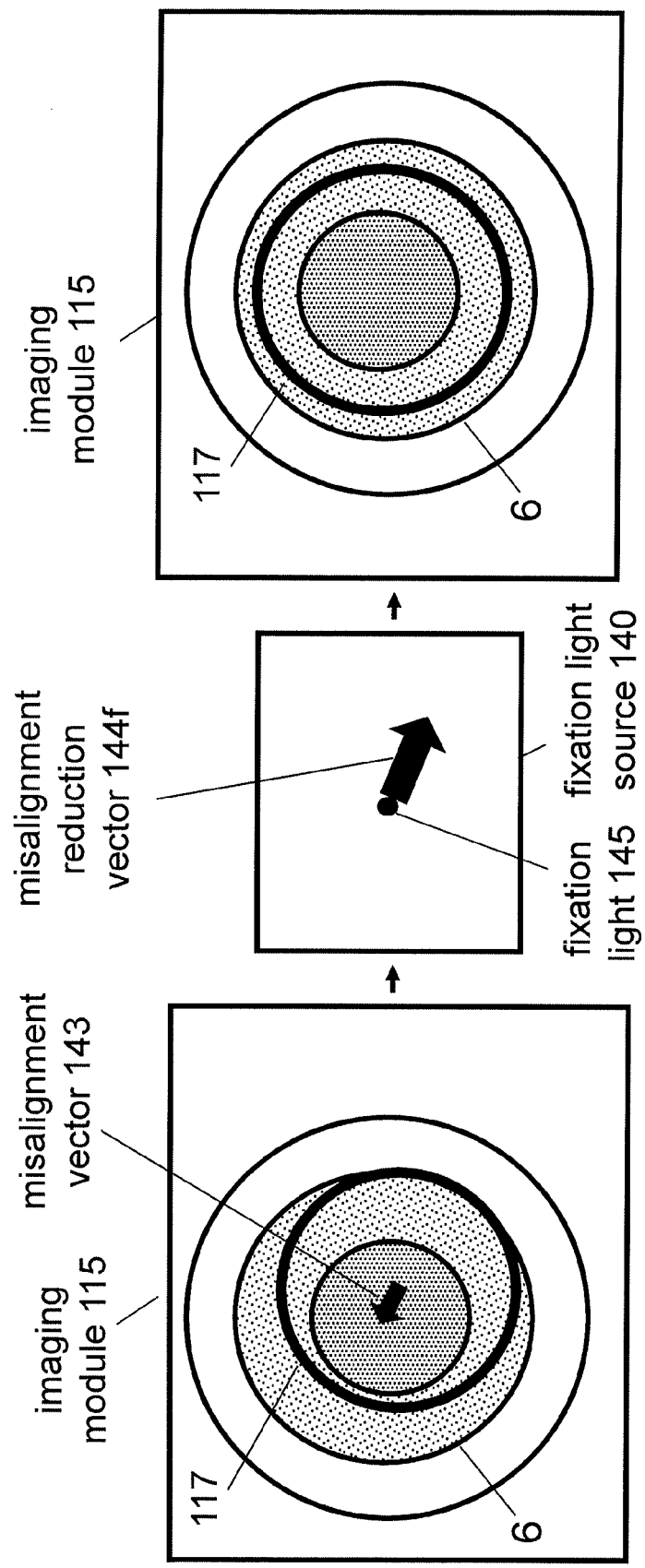

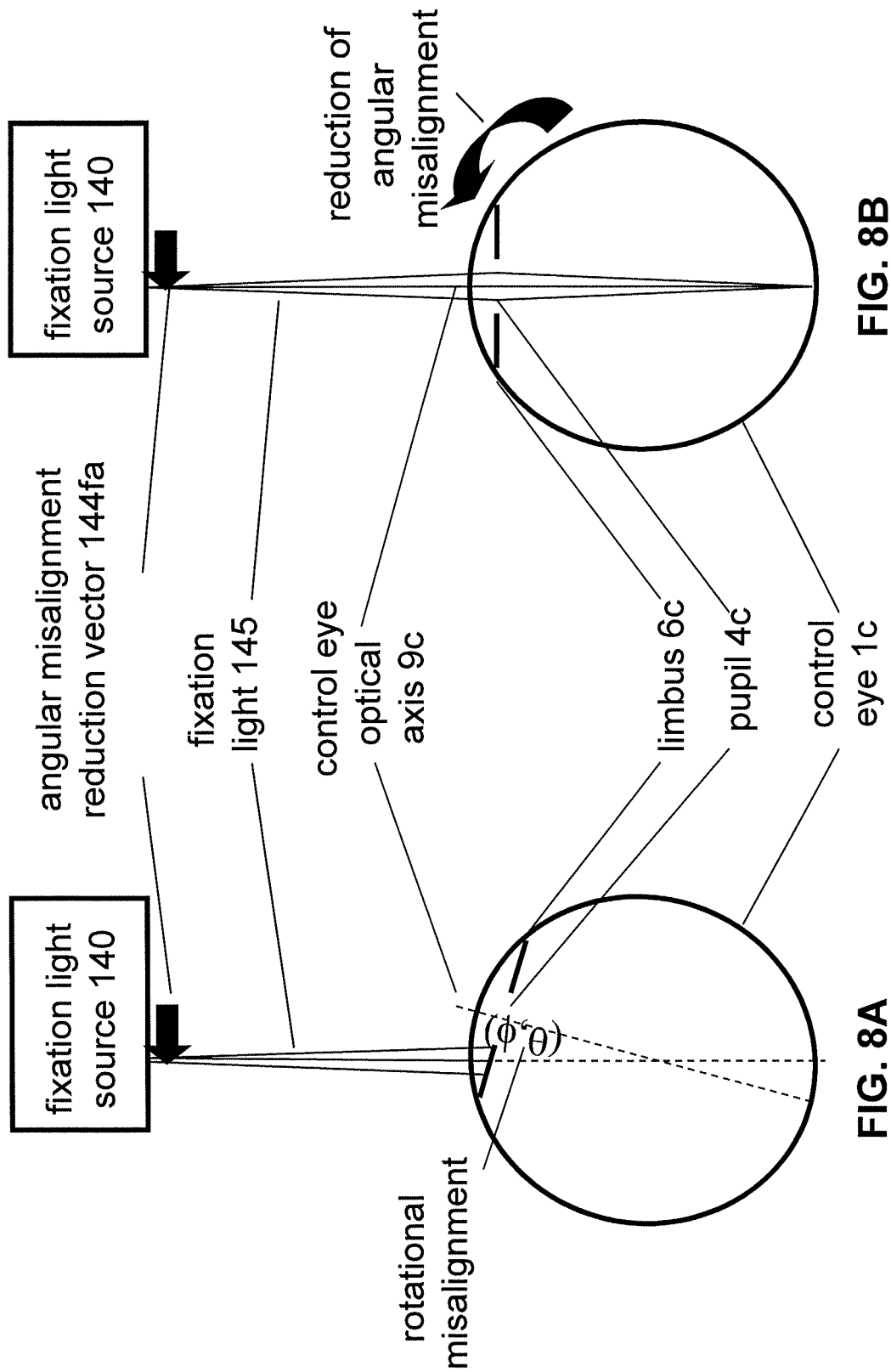

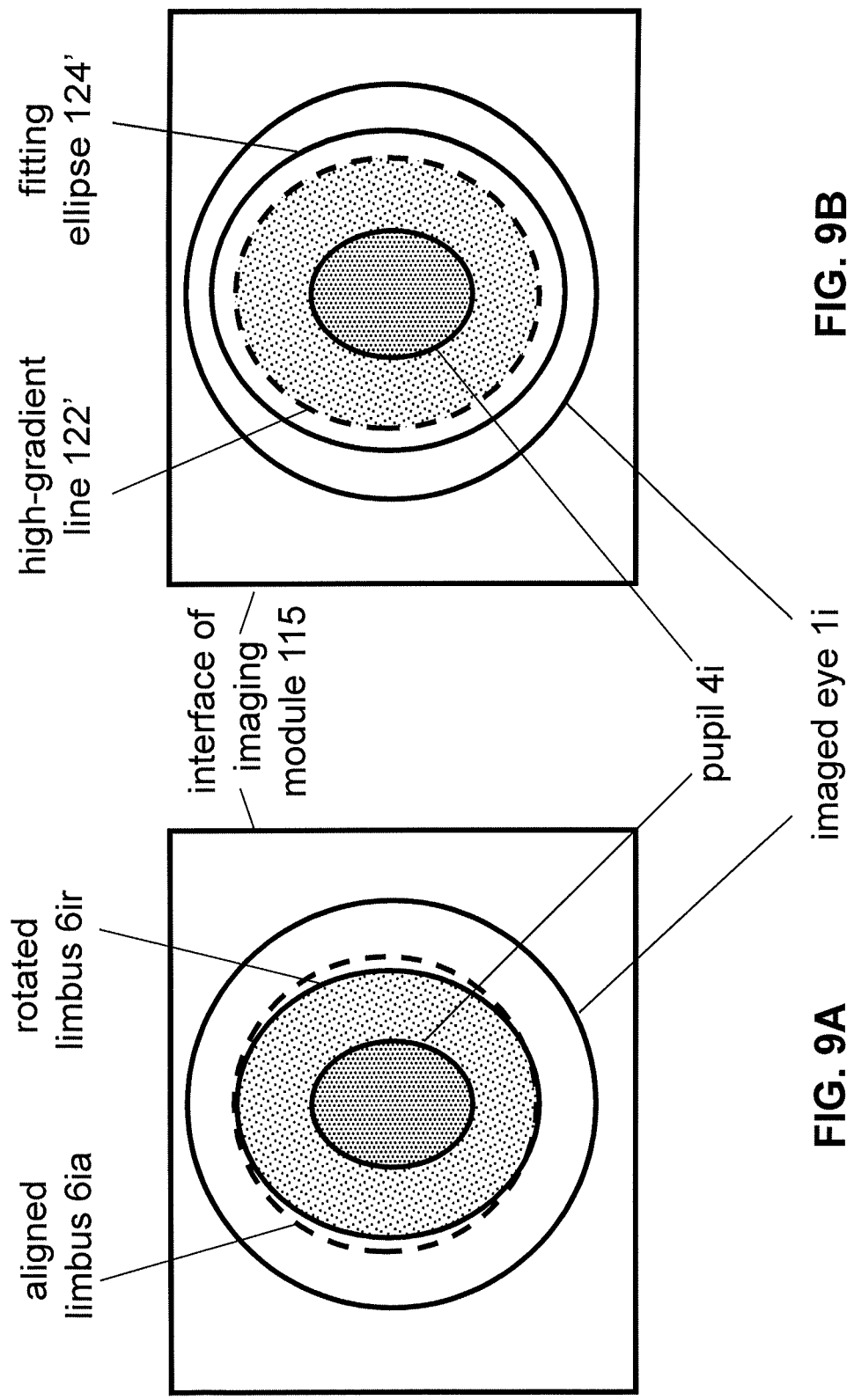

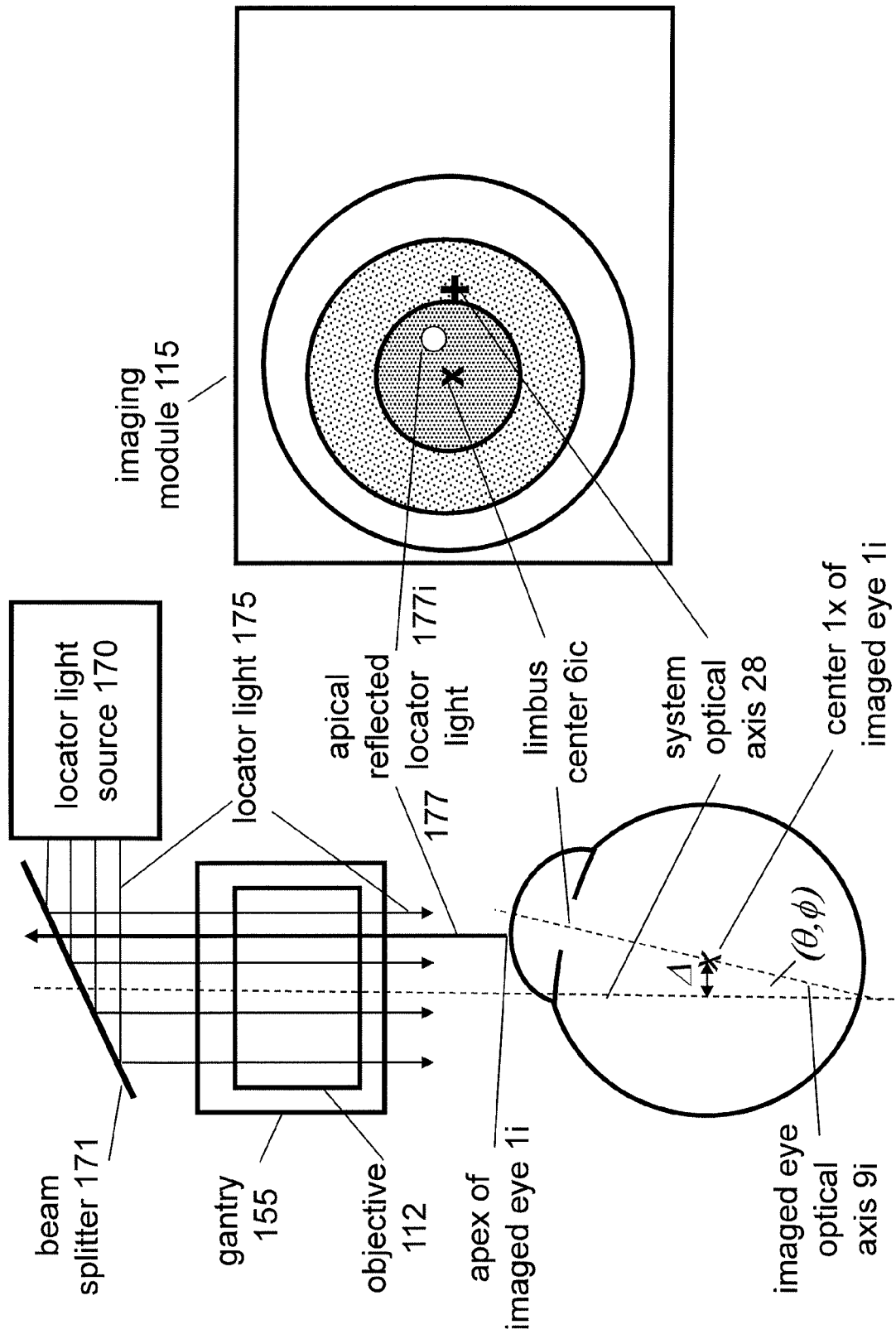

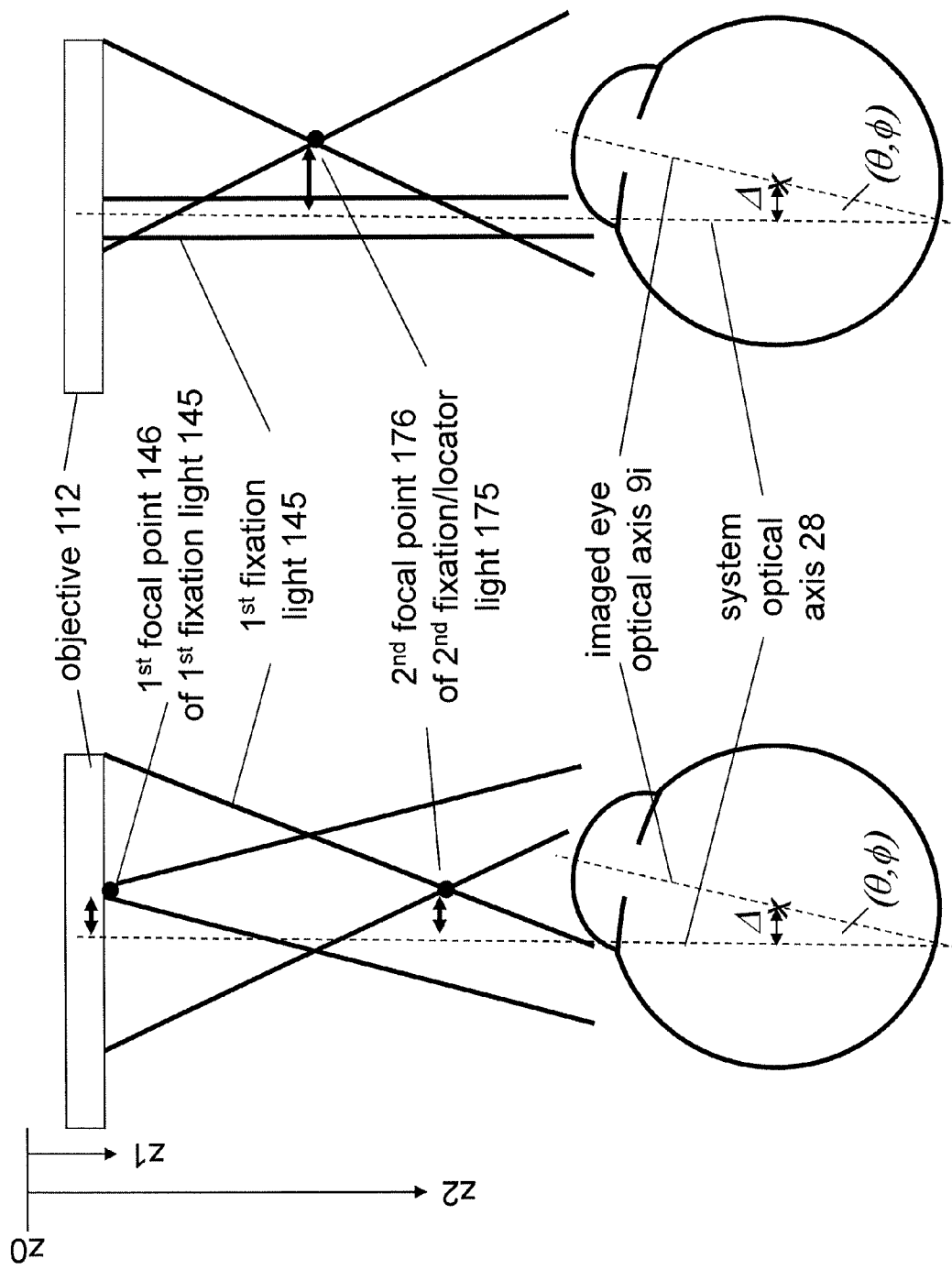

IMAGE-PROCESSOR-CONTROLLED MISALIGNMENT-REDUCTION FOR OPHTHALMIC SYSTEMS

TECHNICAL FIELD

This patent document relates to systems and techniques for ophthalmic imaging. In more detail, this patent document relates to systems and methods for providing an electronically controlled fixation light for improving a precision of aligning or docking an ophthalmic imaging system to a patient's eye.

BACKGROUND

A variety of advanced imaging devices have been developed over the years for ophthalmic imaging, diagnostics and surgery. For some applications, these imaging devices perform best when their optical axis is aligned with an optical axis of the imaged eye. Once the optical axis of the eye is aligned with the optical axis of the imaging device, some imaging devices enhance the precision of the imaging process by immobilizing the eye in the aligned position with the help of a patient interface or eye-docking system. As the precision of the imaging devices improves, the demand for eye-docking systems which provide more precise alignment also increases.

In typical existing systems the alignment is guided manually. The operator can direct the patient verbally, manually orient the eyeball, or adjust portions of the imaging device, such as its objective or gantry, or any combination of the above. These adjustments are performed iteratively during the docking process. However, the inaccuracy of these manual approaches can make the docking process quite time consuming and frustrating, and still fall short of achieving high quality alignment. Because of the limited precision of the manually guided alignment, the patient interface often ends up docked to the eye in an off-center position, the eye's optical axis tilted and the eye laterally misplaced relative to that of the imaging system.

Some imaging systems use guidance mechanisms that promise improvements for the alignment process. In some systems, such as in some surgical systems using excimer lasers, the alignment is aided by a fixation light. The fixation light can be centered with the optical axis of the imaging system. The patient can be instructed to train his eye on the fixation light. This fixation can align the patient's eye with the imaging system. However, even these fixation light systems have limitations.

SUMMARY

This patent document discloses fixation light controller systems with improved functionalities. The eye of the patients typically has both lateral and angular misalignment relative to the imaging system. Simply looking at a fixed fixation light centered with the optical axis of the imaging device does not eliminate both types of misalignments.

Therefore, in some systems, including some YAG lasers and slit lamps, the fixation light is not fixed and can be manually or mechanically adjusted. However, since the adjustment is only mechanical/manual, the precision of these fixation lights is considerably less than the precision of the imaging systems. Further, such mechanical adjustments can be quite time consuming and frustrating because of their limited precision.

Finally, in some systems the fixation light may be controlled in part manually and in part electronically. In the hands of expert surgeons manual operations may improve the alignment, in other cases such system may still lack the required precision.

The present patent document discloses fixation light controller systems that offer solutions for the above described problems. In some implementations, an ophthalmic system may include an ophthalmic imaging device configured to generate an image of a portion of an imaged eye of a patient, an image processor, configured to determine a misalignment of the imaged eye and the imaging device by processing the generated image, and to generate a control signal according to the determined misalignment, and a misalignment-reduction system, configured to receive the control signal, and to generate a misalignment-reduction response.

In some implementations the ophthalmic imaging device can include an electronic sensing system that senses a collected imaging light from the imaged eye, including at least one of a Charge-Coupled Device (CCD) array, a Complementary Metal-Oxide Semiconductor (CMOS) array, a pixel-array, and an electronic sensor array, and an electronic display system that displays the image of a portion of the imaged eye in relation to the sensed collected imaging light, including at least one of a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a high definition (HD) video microscope, a processor-based image system, an opto-mechanical projector of the electronic or digital type, and a light-source movable by an electro-mechanical actuator.

In some implementations the image processor is configured to identify an ophthalmic structure in the image, and to determine a measure of misalignment by determining a location of the ophthalmic structure relative to a reference of the imaging device. In some implementations the image processor is configured to identify the ophthalmic structure by determining a high-gradient line in the image, separating image elements with substantially different brightness or color.

In some implementations the image processor is configured to fit at least one of a circle and an ellipse to the high-gradient line by measuring radial distances between the high-gradient line and the circle or ellipse, to determine a location coordinate of the fitted circle or ellipse by minimizing a measure of the radial distances, and to determine a misalignment-measure by relating the determined location coordinate and a coordinate of the reference. In some implementations the image processor is configured to determine a high-contrast line in the image, to determine misalignment distances between the high-contrast line and a targeting pattern, and to determine a misalignment-measure from the misalignment distances.

In some implementations the reference of the imaging device is at least one of an objective, a patient module, a docking tip, an interface, a contact lens, a pupil, a viewing frame, a reference frame, and an internal lens of the ophthalmic system, and the imaging device is configured to generate a reference pattern related to the reference to assist the image processor to determine the misalignment of the imaged eye and the imaging device. In some implementations the recognized ophthalmic structure is a limbus of the imaged eye. In some implementations at least a portion of the image processed by the image processor is not displayed by the imaging device.

In some implementations the misalignment-reduction system can include a fixation light source, and the misalignment-reduction response comprises the fixation light source generating a fixation light in response to the received control signal. In some implementations the fixation light source is configured to generate the fixation light for a non-imaged eye of the patient, and to move the generated fixation light according to the received control signal to assist a reduction of a misalignment between the imaged eye and a reference-component of the ophthalmic system. In some implementations the fixation light source can include at least one of a LED array, a plasma screen, an electronic display, a computer display, an LCD screen, a video-module, an opto-mechanical projector of the electronic or digital type, a CRT display, a slit-lamp, a processor-based image system, and a light-source movable by an electro-mechanical actuator. In some implementations the fixation light source is configured to generate the fixation light to guide the patient to reduce an angular misalignment.

In some implementations the image processor is configured to determine the angular misalignment by fitting an ellipse to a high-contrast line of the image, and analyzing at least one of an aspect ratio and an area of the fitted ellipse. In some implementations the fixation light source can include a collimator to generate a fixation light to guide the patient to reduce a lateral misalignment.

In some implementations the misalignment-reduction system can include a gantry, configured to move a movable portion of the imaging device, and a gantry controller, configured to receive the control signal from the image processor, and to move the gantry according to the received control signal, and the misalignment-reduction response can include the gantry controller moving the gantry and thus the movable portion of the imaging device to reduce a lateral misalignment. In some implementations the gantry is also part of the ophthalmic imaging device. In some implementations the misalignment-reduction system can include a support-gantry, configured to move a patient support relative to the imaging device, and a gantry controller, configured to receive the control signal from the image processor, and to move the support-gantry according to the received control signal, and the misalignment-reduction response can include the gantry controller moving the support-gantry and thus the patient support to reduce a lateral misalignment.

In some implementations the image processor is configured to determine an angular and a lateral misalignment by processing the image, and the misalignment-reduction system can include only one of a fixation light source and a gantry controller.

In some implementations the image processor is configured to determine an angular and a lateral misalignment by processing the image, and the misalignment-reduction system can include a fixation light source, a gantry and a gantry controller. In some implementations, the image processor is configured to determine an angular and a lateral misalignment by processing the image and a misalignment information.

In some implementations the imaging system can include a locator light source, configured to project a locator light on the imaged eye, and the image processor is configured to identify an apical reflected locator light in the image generated by the imaging device, and to determine the misalignment information by analyzing the apical reflected locator light. In some implementations the misalignment information is at least one of an angular misalignment information, related to a vector in the image between the apical reflected locator light and a location of an imaged ophthalmic structure, and a lateral misalignment information, related to a vector in the image between a reference of the imaging system and at least one of the apical reflected locator light and the location of an imaged ophthalmic structure.

In some implementations the ophthalmic system is configured to reduce the angular misalignment by adjusting the fixation light source, and to reduce the lateral misalignment by operating the gantry controller. In some implementations the fixation light is adjustable so that the locator light and a location of an imaged ophthalmic structure can be aligned by adjusting the fixation light. In some implementations the fixation light source and the locator light source are capable of operating at different wavelengths. In some implementations the locator light is invisible for the imaged eye.

In some implementations a patient interface is configured to dock to the imaged eye of the patient after the misalignment-reduction system executed the misalignment-reduction response. In some implementations the misalignment-reduction system can include a fixation light source, configured to generate a fixation light for the imaged eye of the patient, and to adjust the generated fixation light according to the received control signal to assist a reduction of a misalignment between the imaged eye and a reference-component of the ophthalmic system. Some implementations include a locator light, focusable to a second focal point different from a first focal point of the fixation light.

In some implementations a method of aligning an eye with an ophthalmic system can include generating an image of a portion of an imaged eye of a patient by an ophthalmic imaging device, determining a misalignment of the imaged eye and the imaging device by an image processor processing the generated image, and generating a misalignment-reduction response electronically by a misalignment-reduction system based on the determined misalignment.

In some implementations the determining the misalignment can include identifying an ophthalmic structure in the image, and determining a location of the ophthalmic structure relative to a reference of the imaging device. In some implementations the generating the misalignment-reduction response can include generating a fixation light by a fixation light source according to the determined misalignment.

In some implementations the generating the fixation light can include generating the fixation light to guide the patient to reduce an angular misalignment. In some implementations the generating the fixation light can include generating a fixation light to guide the patient to reduce a lateral misalignment, wherein the fixation light source can include a collimator.

In some implementations the generating the fixation light can include generating the fixation light for a non-imaged eye of the patient, and the generating the misalignment-reduction response can include adjusting the fixation light according to the determined misalignment to assist the patient to reduce the misalignment. In some implementations the generating the fixation light can include generating the fixation light for the imaged eye of the patient, and the generating the misalignment-reduction response can include adjusting the fixation light according to the determined misalignment to assist the patient to reduce the misalignment.

In some implementations the generating the misalignment-reduction response can include moving a gantry of the imaging system by a gantry controller to reduce a lateral misalignment.

In some implementations the determining the misalignment can include determining an angular and a lateral misalignment by the image processor processing the image and a misalignment information, and the generating the misalignment-reduction response can include adjusting a fixation light of a fixation light system and a gantry controller. In some implementations the determining the misalignment can include projecting a locator light onto the imaged eye by a locator light system, locating an apical reflected locator light in the image generated by the imaging device, and determining the misalignment information using the located apical reflected locator light. In some implementations the determining the misalignment information can include determining an angular misalignment information, related to a vector in the image between the apical reflected locator light and a location of an imaged ophthalmic structure, and determining a lateral misalignment information, related to a vector in the image between a reference of the imaging system and at least one of the apical reflected locator light and the imaged ophthalmic structure.

In some implementations the generating the misalignment-reduction response can include reducing the angular misalignment by adjusting the fixation light, and reducing the lateral misalignment by operating the gantry controller. In some implementations the reducing the angular misalignment and the reducing the lateral misalignment are repeated iteratively. In some implementations the generating the misalignment-reduction response can include projecting the fixation light into the imaged eye, and reducing the lateral and the angular misalignment by causing the head of the patient to move laterally to align the locator light and the fixation light.

In some implementations an ophthalmic system can include an imaging device that generates an image of an imaged eye of a patient, an image processor that determines an angular and a lateral misalignment of the imaged eye and the imaging device by processing the generated image, a fixation light system that projects a fixation light on an eye of the patient to assist a reduction of the angular misalignment, and a gantry that adjusts a movable optic of the system to reduce the lateral misalignment. In some implementations the ophthalmic system can include an indicator light system that projects an indicator light on the imaged eye to provide a misalignment information for the image processor.

BRIEF DESCRIPTION OF THE DRAWINGS

FIGS. 6A-B illustrate a fixation light system.
FIGS. 7A-C illustrate a misalignment reduction method.
FIGS. 8A-B illustrate misalignment reduction with a fixation light.
FIGS. 9A-B illustrates an image processing method to determine an angular misalignment.
FIGS. 17A-B illustrate a locator light system processing an angular and a lateral misalignment.

FIGS. 20A-B illustrate a system with two fixation lights.

DETAILED DESCRIPTION

Implementations and embodiments in this patent document provide a fixation light system for ophthalmic imaging devices for increasing the precision of the alignment of the imaged eye and the imaging device.

Figure 1:
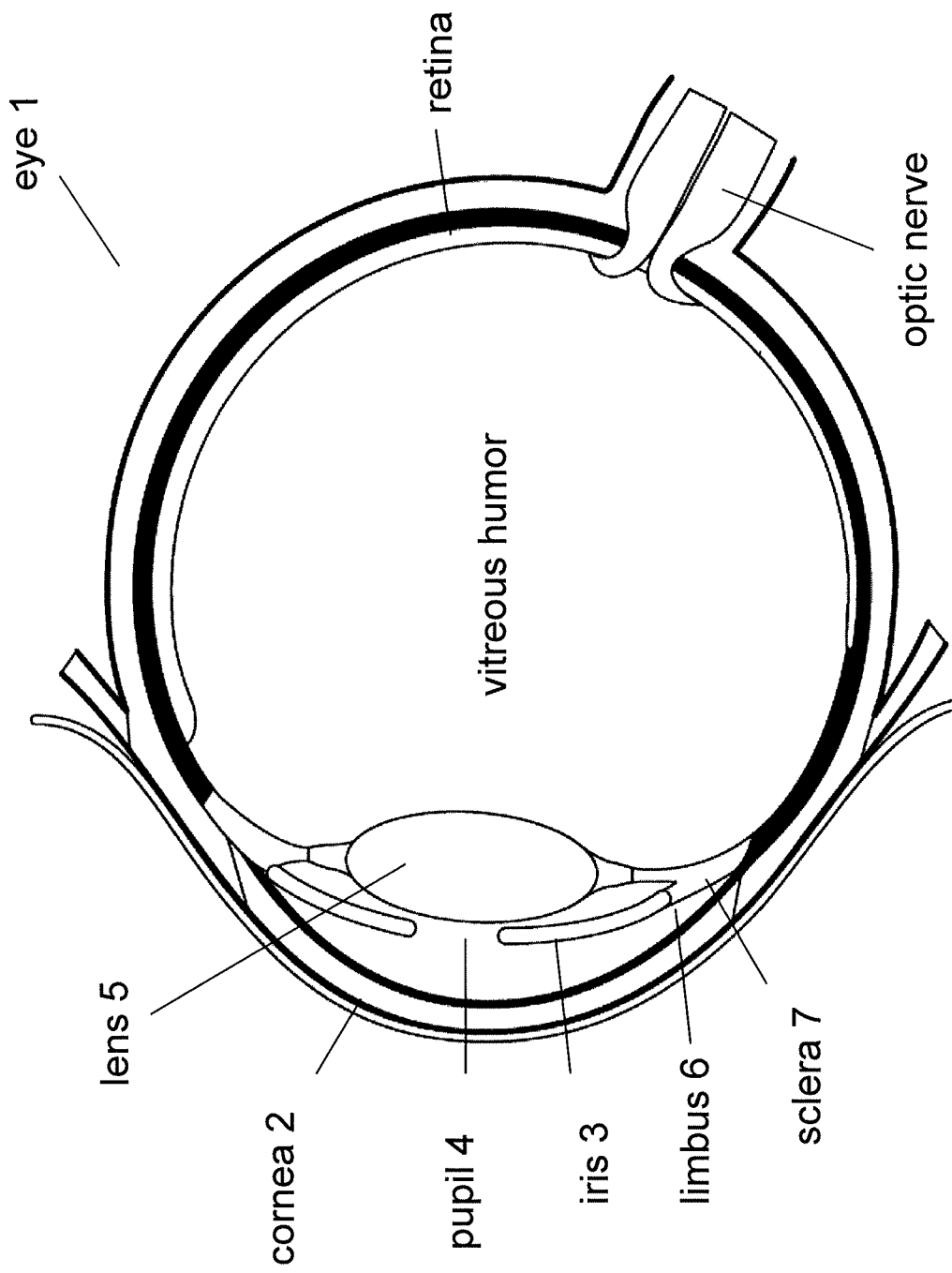
FIG. 1 illustrates an eye.

FIG. 1 illustrates a human eye 1 in some detail. The eye 1 includes a cornea 2 that receives and refracts the incoming light, an iris 3, a pupil 4, in effect an opening for the light to enter the inner eye, and a lens 5 that focuses the light on the retina. In addition, the eye 1 includes a limbus 6, delineating the boundary between the colored iris 3 and a white sclera 7.

Figure 2:
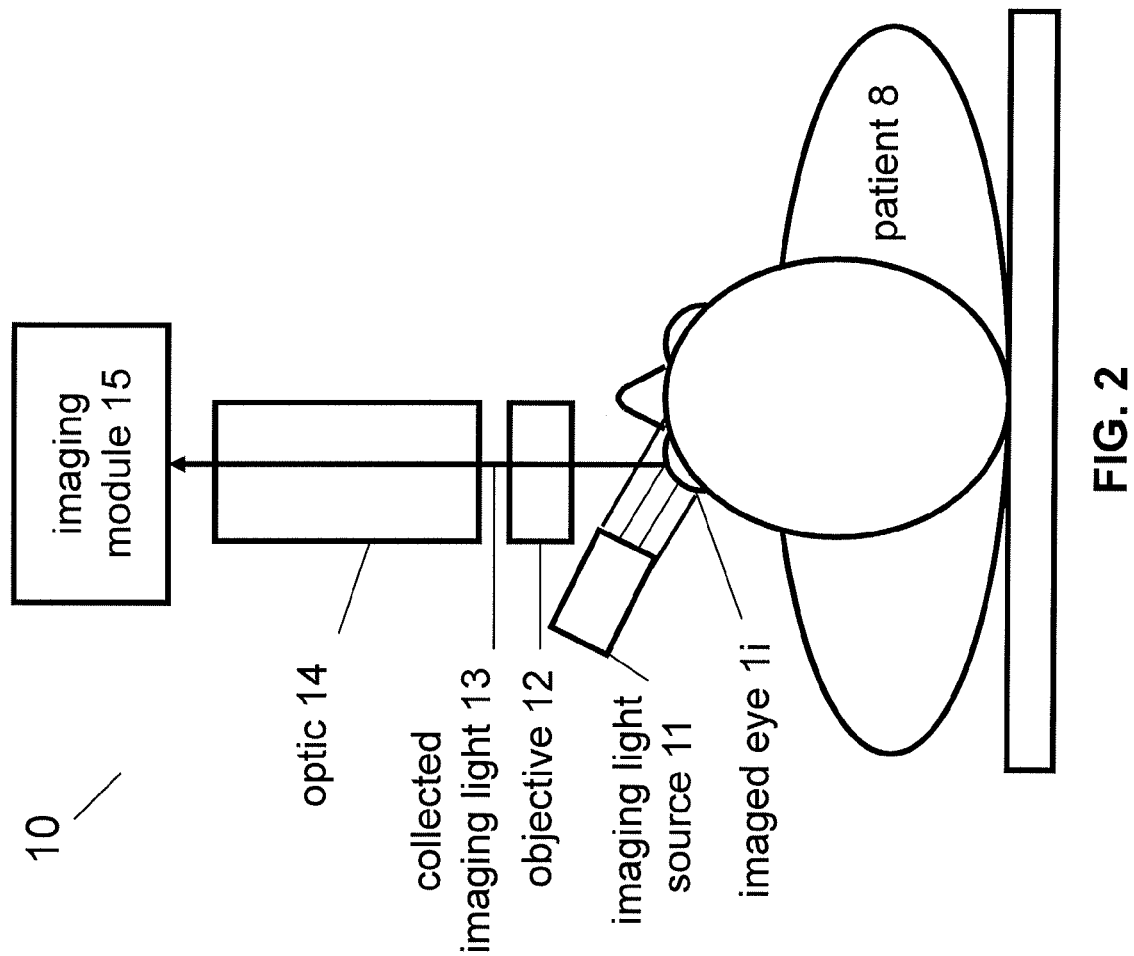
FIG. 2 illustrates an ophthalmic imaging system.

FIG. 2 illustrates an ophthalmic imaging system 10 and its operation. A patient 8 can be laid on a supporting bed. An imaging light source 11 can shine an imaging light on an imaged eye 1i. A portion of the imaging light reflected by the imaged eye 1i can be collected by an objective 12 and guided as a collected imaging light 13 to an optic or optical system 14. The optic 14 can guide the collected imaging light 13 to an imaging module 15. A surgeon or medical professional can analyze the image provided by the imaging module 15 and give instructions to the patient to move the imaged eye 1i to improve its alignment with an optical axis of the imaging system 10. In other cases, the surgeon can manipulate the imaged eye 1i manually to improve the alignment. These steps can be practiced to prepare the imaged eye 1i for docking a patient interface to it, or just simply to align the eye with the imaging system 10 better. The patient interfaces can be used either to assist the imaging the eye 1i, or for performing an ophthalmic surgical procedure. In other systems, a non-contact imaging procedure can be performed after the alignment. In yet other systems, the alignment can be followed by a diagnostic procedure. In any of the above described systems the ophthalmic imaging system 10 provides the surgeon only with an image of limited precision as the alignment with the eye is only approximate.

Figure 3A:
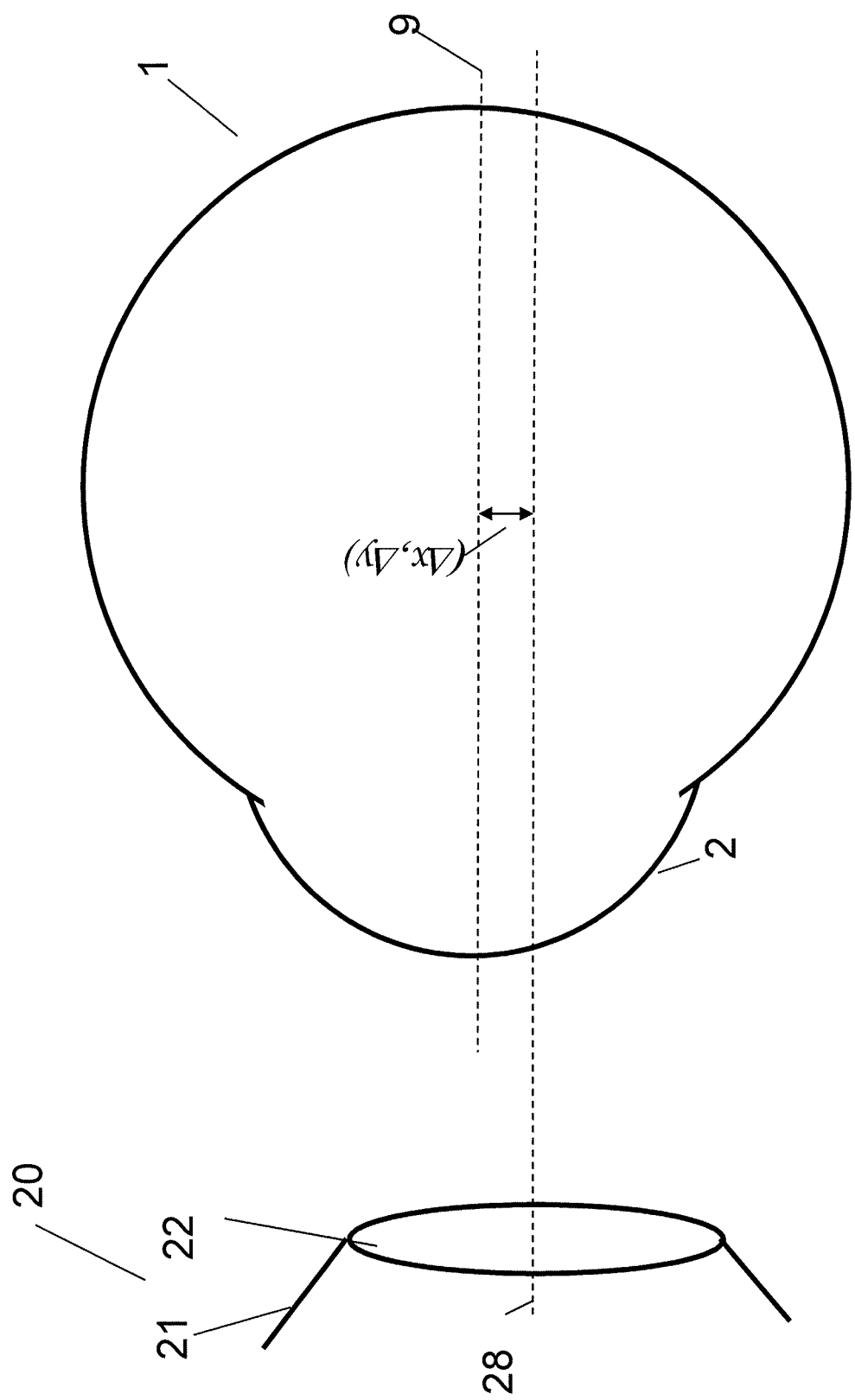
FIGS. 3A-C illustrate misalignments of the eye.
Figure 3B:
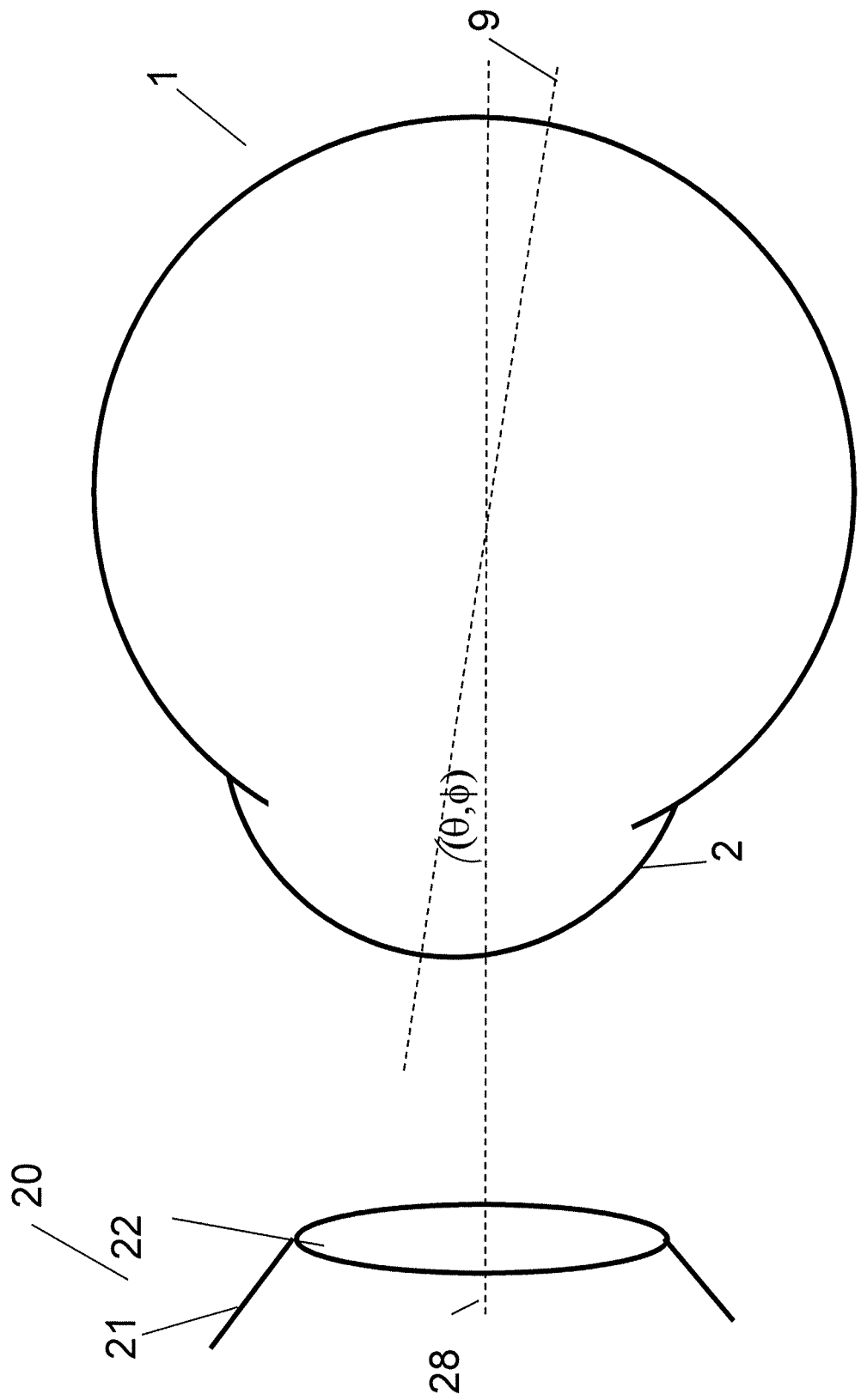

FIGS. 3A-B illustrate that after the use of such a limited precision ophthalmic imaging system 10, a residual misalignment between the eye 1 and the ophthalmic imaging system 10 can persist. In detail, a distal end 20 of the ophthalmic system 10 can be the objective 12, or a contact module, a docking unit, a distal tip, an interface, or an applanation module. In any of these designs, the distal end 20 can include a housing 21 that supports a distal lens 22. An optical axis 28 of the ophthalmic imaging system 10, typically shared with an optical axis of the distal lens 22, can remain misaligned with an optical axis 9 of the eye 1 even after the above limited-precision docking procedure has been performed.

FIG. 3A illustrates that the misalignment can be a lateral misalignment characterized by a (Δx, Δy) vector between the optical axis 9 of the eye and the optical axis 28 of the imaging system 10, lying approximately in the lateral plane perpendicular to the optical axis 28.

FIG. 3B illustrates that the misalignment can also be an angular misalignment. In general, the angular misalignment can be characterized by the (θ, φ) Euler angles between the optical axis 9 of the eye and the optical axis 28 of the imaging system 10. In many cases, the misalignment can be a combination of a lateral and an angular misalignment.

Figure 3C:
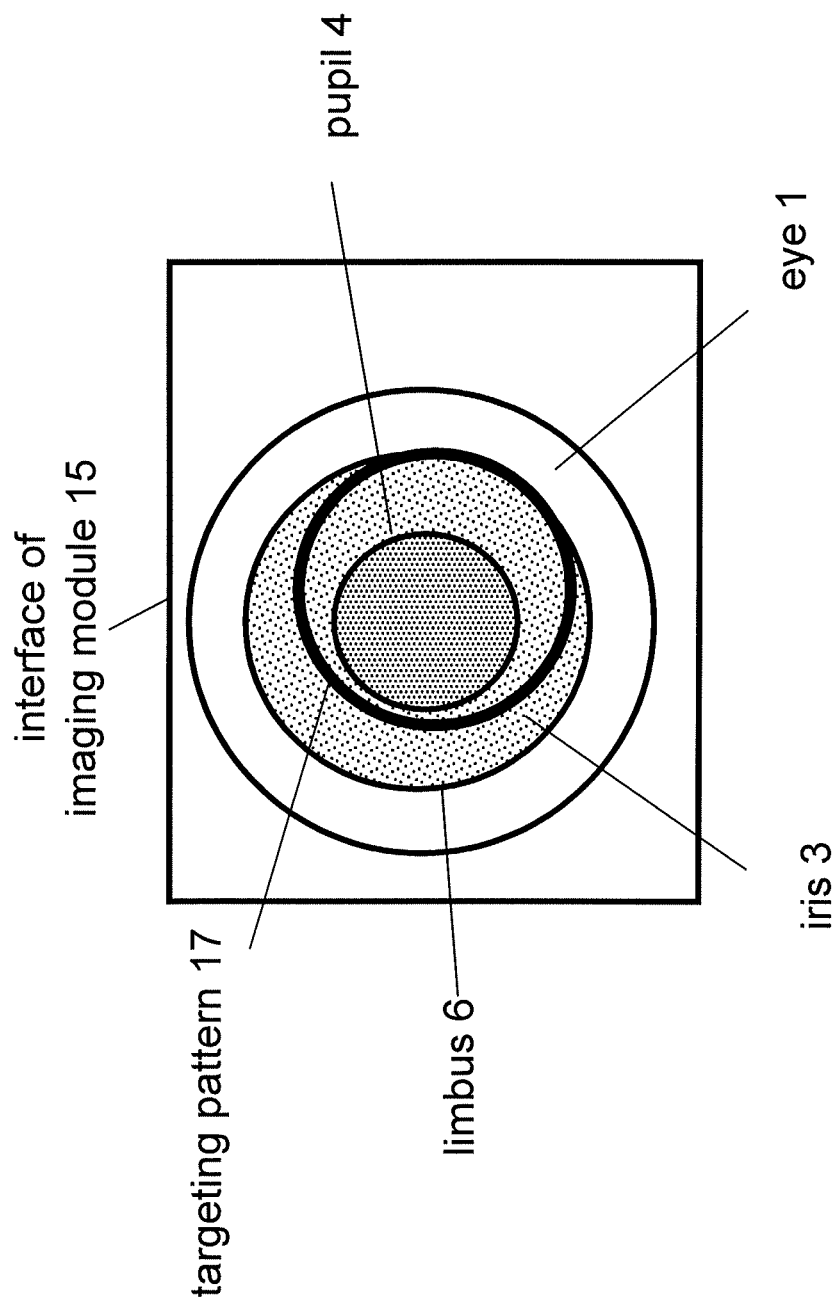

FIG. 3C illustrates that on an imaging interface of the imaging module 15 either misalignment can appear as a displacement of the iris 3 and pupil 4 relative to a targeting pattern 17, such as a target circle. The surgeon can give verbal instructions to the patient to move the imaged eye 1i, or to manipulate the eye 1i manually based on this displayed displacement.

However, verbal instructions can be unclear to an already disoriented patient, and manipulating the eye can be cumbersome and imprecise. Also, the patient is likely to undo or resist the actions of the surgeon or technician.

Some ophthalmic systems can utilize a fixation light to provide guidance for the patient. However, fixation light devices still have shortcomings as discussed above. Some devices provide adjustable fixation lights as an improvement. However, even in such systems, the location of the fixation light is typically adjusted manually or mechanically, still resulting in an adjustment process with limited precision.

Figure 4:
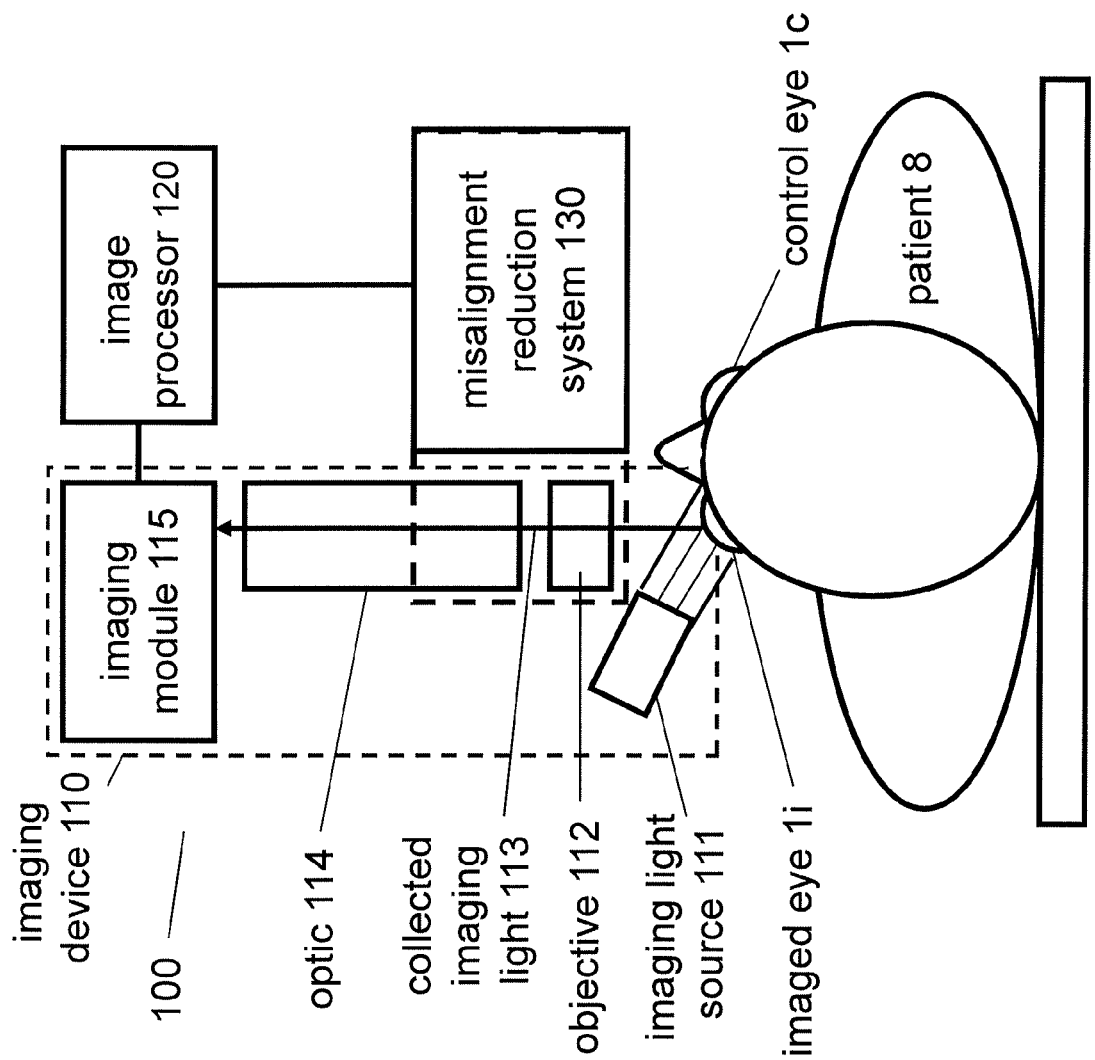
FIG. 4 illustrates an ophthalmic system with a misalignment reduction system.

FIG. 4 illustrates an ophthalmic imaging system 100 that can be used to align the imaged eye 1i and the ophthalmic system 100 with improved precision. The ophthalmic system 100 can include an ophthalmic imaging device 110, an image processor 120 and a misalignment reduction system 130. The ophthalmic imaging device 110 can be configured to generate an image of a portion of an imaged eye of a patient. The image processor 120 can be configured to determine a misalignment of the imaged eye and the imaging device by processing the generated image, and to generate a control signal according to the determined misalignment. The misalignment-reduction system 130 can be configured to receive the control signal and to generate a misalignment-reduction response.

The ophthalmic imaging device 110 can include an imaging light source 111 that provides an imaging light for the imaged eye 1i. The imaging light source 111 can be a single light, a ring of e.g. 4, 6 or 8 lights, or a light source with a continuous ring shape. An objective 112 can collect a fraction of the imaging light, returned by the imaged eye 1i, and direct it as a collected imaging light 113 to an optic 114. The optic 114 can guide the collected imaging light 113 towards an imaging module 115. In general, the optic 114 can be quite complex, including a large number of lenses and mirrors. The optic 114 can also be multifunctional, for example also configured to guide a surgical laser beam to the imaged eye 1i. The imaging module 115 can provide an image for an operator of the imaging system 100 via an imaging interface.

In some implementations, the ophthalmic imaging device 110 can include a microscope, an ophthalmic microscope, or a stereo microscope. An imaging interface of these microscopes can include the eyepiece of these microscopes.

In some implementations, the ophthalmic imaging device 110 can generate the image at least in part electronically. For example, the imaging module 115 of the ophthalmic imaging device 110 can include an electronic sensing system that senses the collected imaging light 113. The electronic sensing system can include a Charge-Coupled Device (CCD)-array, a Complementary Metal Oxide Semiconductor (CMOS) array, a pixel-array, or an electronic sensor array to sense the collected imaging light 113.

In these electronic imaging systems the imaging module 115 can also include an electronic display system as an imaging interface. This electronic display can display an electronic image of a portion of the imaged eye 1i based on the sensed light 113. This electronic display or imaging interface can be, for example, a Light Emitting Diode (LED), an organic LED (OLED) display, an active matrix OLED (AMOLED) display, a plasma screen, an electronic display, a computer display, a Liquid Crystal Display (LCD) screen, a Cathode Ray Tube (CRT) display, a video-module, a video microscope display, a stereo video microscope display, a High Definition (HD) video microscope, a processor-based image system, an opto-mechanical projector of the electronic or digital type, or a light-source movable by an electro-mechanical actuator. In some implementations, the above elements of the imaging systems can be combined.

Figure 21:
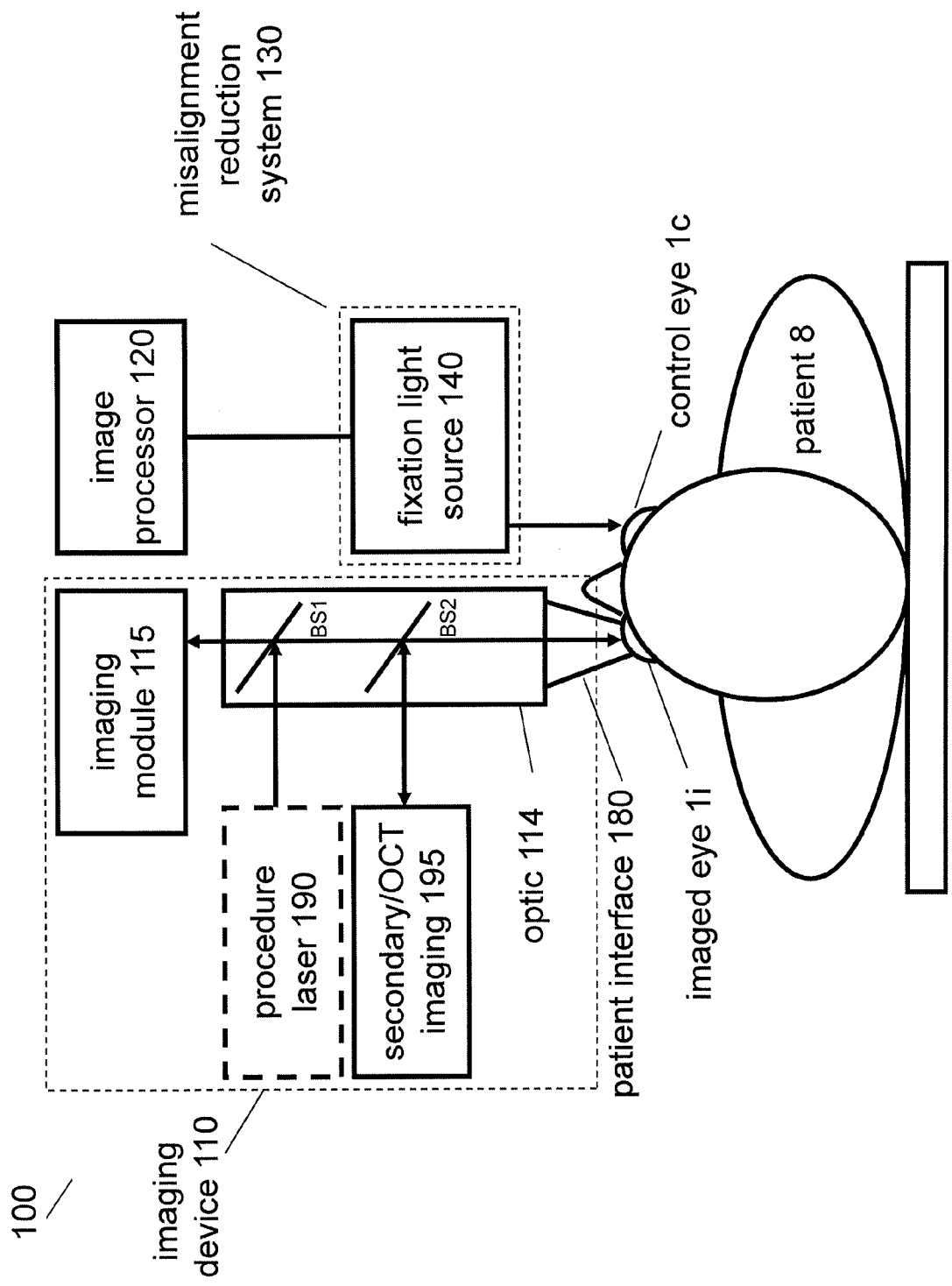
FIG. 21 illustrates a system with an additional OCT imaging system.

In some implementations, the ophthalmic imaging device 110 can include an optical coherence tomographic (OCT) imaging system, as described in relation to FIG. 21.

In some implementations, the misalignment reduction system 130 may include the objective 112, in others portions of the optic 114.

The image processor 120 can be configured to identify an ophthalmic structure in the image, generated by the imaging device 110, and to determine a location of the ophthalmic structure relative to a reference of the imaging device. The reference of the imaging device can be the objective 112, a patient module, a docking tip, an interface, a contact lens, a pupil, a viewing frame, a reference frame, and an internal lens of the ophthalmic system. The imaging module 115 can be configured to generate a reference pattern related to the reference to assist the image processor to determine the misalignment of the imaged eye and the imaging device. A targeting circle similar to the targeting pattern 17 can be such a reference pattern. Other reference patterns may include cross hairs, multiple circles and their combinations.

The image processor 120 may be configured to recognize the limbus 6 as the ophthalmic structure. The image processing may be based on the pupil 4 as well, but often the limbus 6 forms a more regular circle and thus is well suited for the image processing.

FIGS. 5A-E illustrate that in operation, the image processor 120 can first identify one or more ophthalmic structures of the imaged eye 1i e.g. by analyzing the contrast or gradient of the nearby pixels of the image.

Figure 5A:
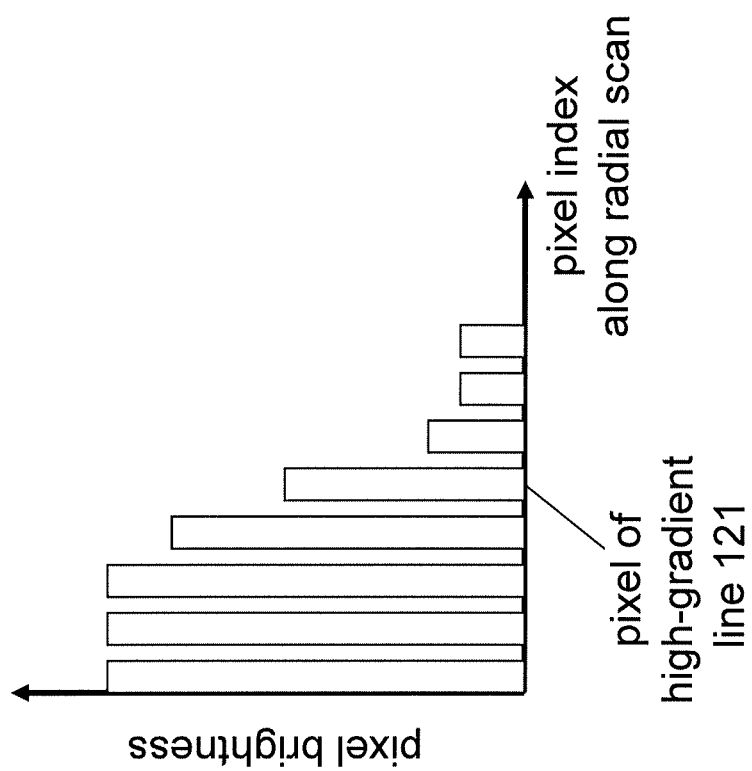
FIGS. 5A-E illustrate an image processing system.

FIG. 5A illustrates that the image processor 120 may perform a radial scan of the image and record the pixels' brightness, color or both along the scan. The center of the radial scan can be chosen in different ways. Also, non-radial scans, such as circular, linear, rectangular, mesh-type, 2D and many other types of scans can be used.

Next, the image processor 120 can identify a high-gradient or high-contrast pixel 121 along the scan as the pixel where the recorded brightness or color varies the fastest. A high-contrast or high-gradient line 122 can be defined by connecting the high-gradient/contrast pixels of nearby scans. Such a high-gradient/contrast line can separate ophthalmic regions with strongly differing brightness or color and thus can be a useful indicator of ophthalmic structures, such as the limbus 6 or the pupil 4. Numerous other methods of machine-vision and image processing are known in the arts to determine structures and their boundaries, which can be used in place of the above described high-gradient/contrast method.

Figures 5B, 5C:
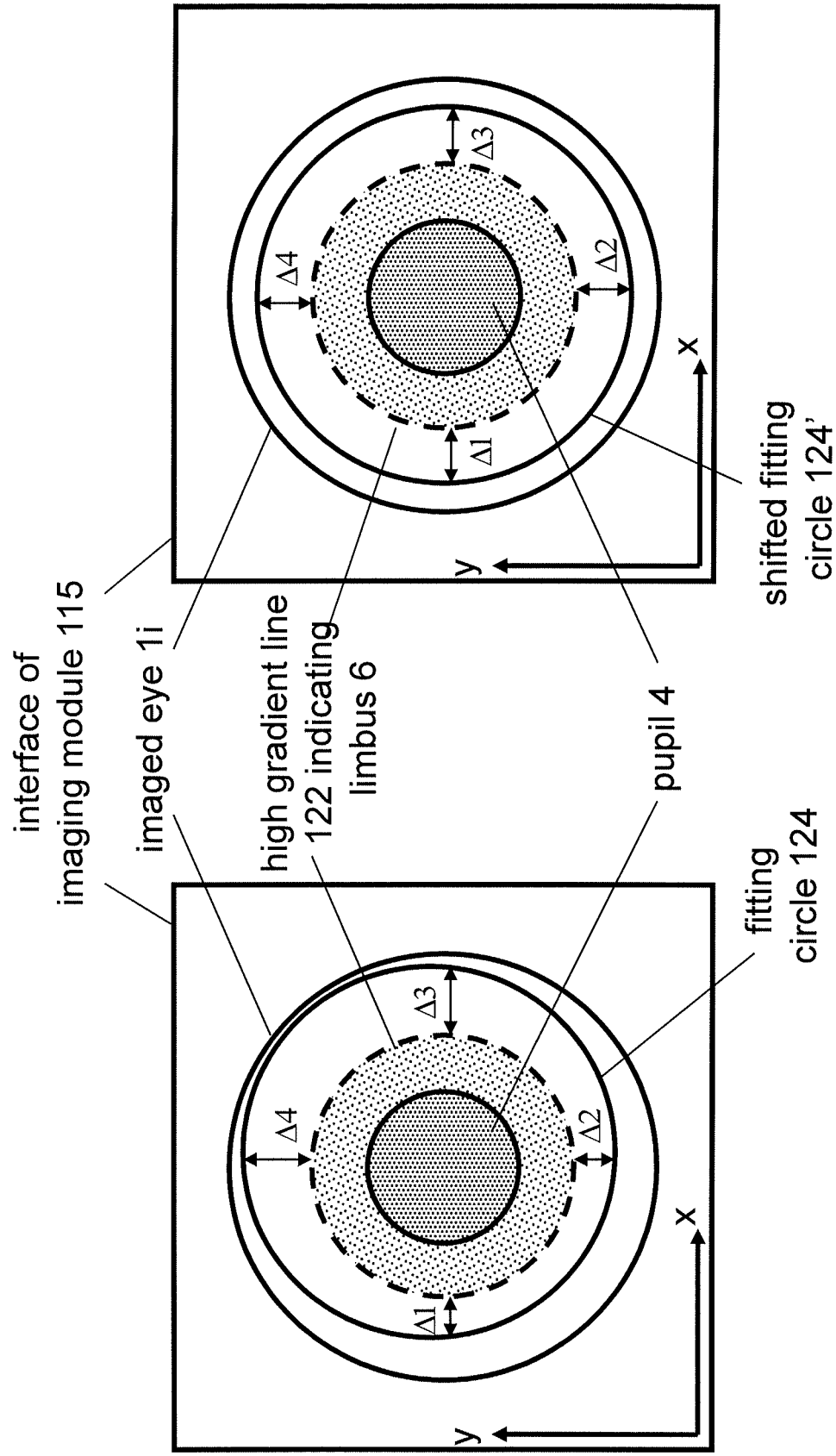

FIG. 5B illustrates that subsequently the image processor 120 can fit probe-functions, such as fitting circles 124 or ellipses to the identified high-gradient/contrast lines to identify circular ophthalmic structures, such as the limbus 6 or the pupil 4. The fitting can take several forms. In some cases, the center and radius of the fitting circle 124 can be moved so that the fitting circle overlays the high-gradient/contrast line with the highest precision. The precision can be quantified e.g. by defining a magnitude of the average radial distance $\Delta$ as the square-root of the average of the squared radial distances between the fitting circle 124 and the high-gradient/contrast line 122 along a preset number of rays, such as 4, 6, or 8 rays. This magnitude of the average radial distance $\Delta$ can be varied by moving around the coordinates (Cx,Cy) of the center of the fitting circle 124 controlled by a search algorithm. Here, the (x,y) coordinate system can be affixed e.g. to the reference system of the interface of the imaging module 115. FIG. 5B illustrates a 4-ray implementation, where the average radial distance is defined as $$\Delta = [(\Delta 1^2 + \Delta 2^2 + \Delta 3^2 + \Delta 4^2)/4]^{1/2}$$

FIG. 5C illustrates that when the search algorithm reaches a minimum of the average radial distance $\Delta$ by shifting the coordinates (Cx,Cy) of the center of the fitting circle 124', the shifted fitting circle 124' becomes essentially concentric with the ophthalmic structure, defined by the high-gradient/contrast line 122. This can be seen e.g. from the symmetry of the individual radial distances: $\Delta 1 = \Delta 2 = \Delta 3 = \Delta 4$. Correspondingly, the center coordinates (Cx,Cy) of the shifted fitting circle 124' essentially coincide with the coordinates (Ox,Oy) of the center of the ophthalmic structure, corresponding to the high-gradient/contrast line 122. This approach can be terminated when the shifted fitting circle 124' becomes concentric with the ophthalmic structure 122, but the radii of the two structures remain different.

Figures 5D, 5E:
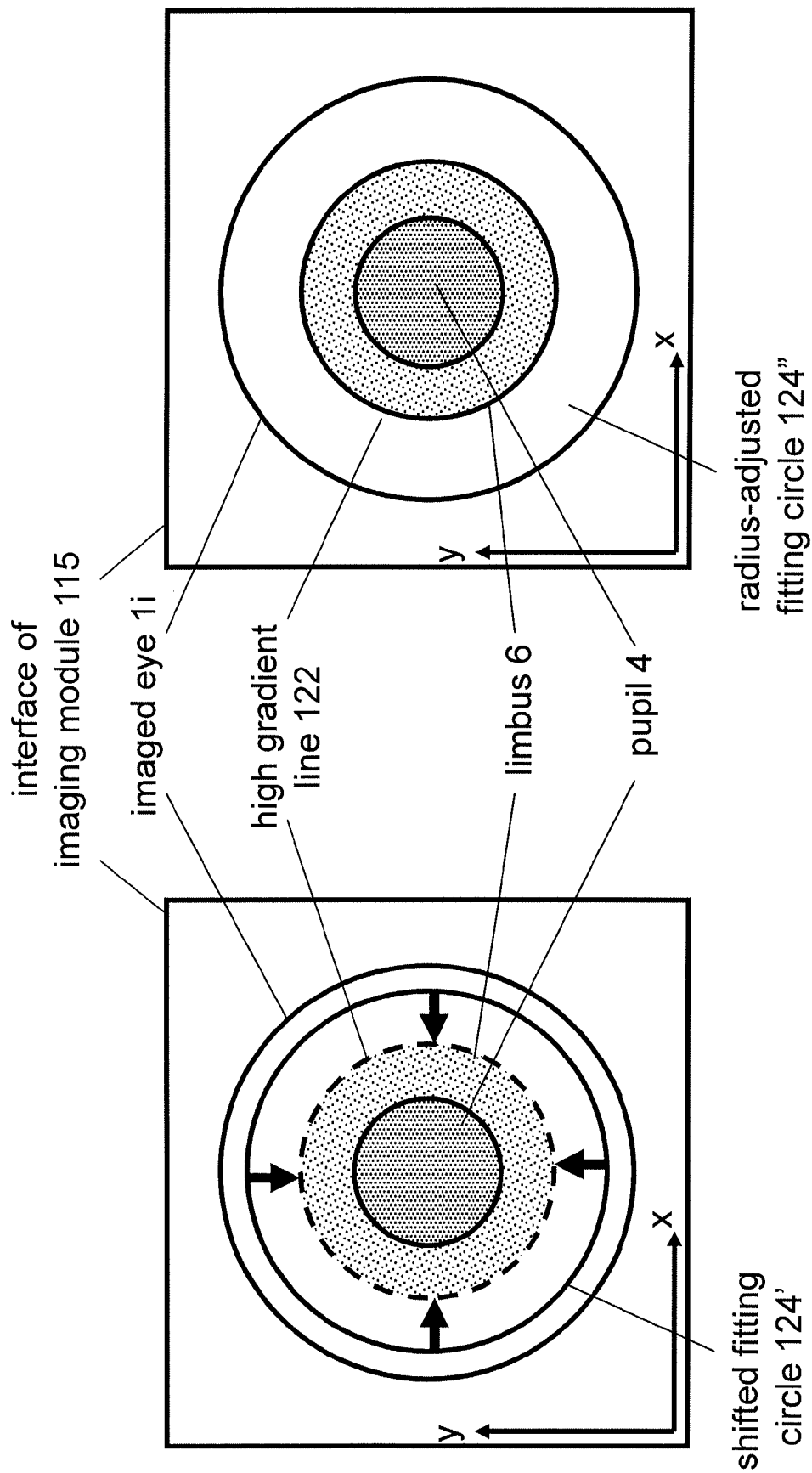

FIGS. 5D-E illustrate that some implementations can also determine the radius of the ophthalmic structure by continuing the search after the concentric state is reached by adjusting the radius of the shifted fitting circle 124' until the global minimum $\Delta(\min)$ is found. For precisely circular structures it may be possible to reach the $\Delta(\min)=0$ absolute global minimum. Once the global minimum $\Delta(\min)$ is reached, the radius of the radius-adjusted fitting circle 124" is essentially equal to the radius of the ophthalmic structure, such as the limbus 6.

In a typical case, the image processor 120 may be able to fit a fitting circle 124 to the high-gradient/contrast line 122 with or without adjusting its radius and thus conclude that the ophthalmic structure indicated by the high contract line 122 is circular. Next, the image processor 120 may determine that the color of the pixels changes from white to non-white across the high-gradient/contrast line 122. These findings can be sufficient for the image processor 120 to conclude that it identified the circular limbus 6 of the imaged eye 1i.

During this fitting process the image processor 120 determines the coordinates of the center of the limbus 6, since the limbus 6 is concentric with the shifted fitting circle 124' and thus the center of the limbus 6 is located at the same (Cx,Cy) coordinates as the center of the shifted fitting circle 124'. Therefore, the image processor 120 can determine a misalignment vector 143 that connects the (Cx,Cy) coordinates of the center of the limbus 6 to the known center coordinates of a targeting pattern 117. The misalignment vector 143 may be used by a misalignment reduction system 130 to reduce the misalignment of the imaged eye 1i with the ophthalmic system 100 as described below.

FIGS. 6A-B illustrate an implementation of the ophthalmic imaging system 100 where the misalignment reduction system 130 includes a fixation light source 140. The fixation light source 140 can project a fixation light 145 into a non-imaged control eye 1c of the patient 8. The patient 8 can be instructed to focus on or follow the fixation light 145 with the control eye 1c. The misalignment reduction response of the misalignment reduction system 130 can be an adjustment of the fixation light 145.

FIG. 7A illustrates that the imaging module 115 can assist the determination of a misalignment of the imaged eye 1i and a reference-component of the ophthalmic imaging device 110 by simultaneously displaying an image portion of the imaged eye 1i and the reference or targeting pattern 117, such as a target circle, via its imaging interface.

The reference-component of the imaging device 110 can be the objective 112, a patient module, a docking tip, an interface, a contact lens, a pupil, a viewing frame, a reference frame, an internal lens of the ophthalmic system, or any equivalents.

The location or display of the targeting pattern 117 can be fixed to the reference-component, in effect indicating the position of the reference-component. Therefore, the simultaneous display of the image portion of the imaged eye 1i and the targeting pattern 117 by the imaging module 115 can effectively assist the determination of the misalignment of the imaged eye 1i.

The image processor 120 can analyze the simultaneously displayed image portion of the imaged eye 1i and the target pattern 117 and compute the misalignment. The details of computing the misalignment were described above extensively. The image processor 120 can summarize the computed direction and magnitude of the misalignment by generating the misalignment vector 143. Based on this misalignment vector 143, the image processor 120 can compute a misalignment reduction vector 144 to be used by the misalignment reduction system 130 to reduce or eliminate the computed misalignment. In general, the misalignment reduction vector 144 need not be the same or simply opposite as the misalignment vector 143, as it represents how the misalignment reduction system is to be adjusted to reduce or eliminate the misalignment. As such, the misalignment reduction vector 144 also depends on the distance of the misalignment reduction system 130 from the eye 1 and on other factors and thus can refer to a large variety of misalignment reduction measures.

Next, the image processor 120 can generate a fixation light control signal for the fixation light source 140 according to the determined misalignment reduction vector 144.

In some implementations, the image of the eye portion and the targeting pattern 117 are not necessarily displayed. Rather, they can be provided for the image processor 120 by the imaging device 110 in an electronic form only, invisible for the system operator or surgeon.

Some image processors 120 do not utilize the fitting circle 124 of FIGS. 5B-E. Instead, these implementations can (a) directly determine misalignment distances $\Delta^*1 \ldots \Delta^*n$ between the high-contrast line 122 and the targeting pattern 117 along n rays, as described above, where n is an integer; and (b) perform a search algorithm to find a misalignment of the ophthalmic structure corresponding to the high-contrast line 122 relative to the targeting pattern 117 or another reference of the imaging system 100. A difference to the previously described method is that in the present method the targeting pattern 117 is centered to the imaging device 110, whereas in the previous systems in an intermediate step the fitting circles 124 were shifted to be concentric with the ophthalmic structure and then the misalignment of the fitting circle was determined relative to the targeting pattern 117.

The search algorithm can be based e.g. on minimizing a misalignment-measure, such as the average misalignment $\Delta$ above, or on symmetrizing the misalignment distances $\Delta^*1 \ldots \Delta^*n$ in opposing directions, among others. After the search, the misalignment vector 143 can be determined to characterize the misalignment. The image processor 120 can then compute the misalignment reduction vector 144 based on the determined misalignment vector 143 and output a fixation light control signal towards the fixation light source 140 corresponding to the misalignment reduction vector 144.

FIG. 7B illustrates that the fixation light source 140 can receive the fixation light control signal and generate, project, or display a fixation light 145 according to the received fixation light control signal. For example, if the misalignment of the imaged eye $1i$ was in the upper-left direction in the reference frame of the imaging system 110, as shown by the misalignment vector 143 in FIG. 7A, the image processor 120 can compute the misalignment reduction vector $144f$ by which the fixation light 145 is to be adjusted to the lower right direction so that if the control eye $1c$ follows the adjusted fixation light 145, the misalignment 143 of the imaged eye $1i$ will be substantially reduced, or optimally even eliminated.

The fixation light source 140 can first generate and display the fixation light 145, and then move the displayed fixation light 145 according to the received fixation light control signal. Since the movements of the control eye $1c$ and the imaged eye $1i$ closely track each other, as the control eye $1c$ is moved by the patient according to the displayed fixation light 145, the imaged eye $1i$ moves in a correlated manner. Because of this correlation between the movements of the imaged eye $1i$ and the control eye $1c$, the fixation light system 120 can assist the reduction of the misalignment of the imaged eye $1i$ relative to the ophthalmic imaging system 110.

Other embodiments may simply display the fixation light 145 by the fixation light source 140 at a properly chosen location according to the fixation light control signal, instead of moving it. In either of these embodiments, the patient can be instructed to follow, or focus on, the fixation light 145 with the control eye $1c$.

The fixation light source 140 can include a LED array, a plasma screen, an electronic display, a computer display, an LCD screen, a video-module, an opto-mechanical projector, a slit-lamp, a processor-based image system, or a light-source, movable by an electro-mechanical actuator.

FIG. 7C illustrates that after the patient followed the adjustment of the fixation light 145 with the control eye $1c$, the imaged eye $1i$ can become essentially centered with the targeting pattern 117 and thus aligned with the optical axis 28 of the imaging system 100. Implementations may not adjust the radius of the targeting pattern 117 to fit the radius of the limbus 6, thus these circles may appear only concentric, but not overlaid.

FIG. 6B illustrates the appearance of the ophthalmic system 100 for the patient 8 in some embodiments. The left panel shows that the imaged eye $1i$ can see the objective 112, surrounded by e.g. six imaging light sources 111. The right panel shows that the non-imaged/control eye $1c$ can see the fixation light 145 displayed on the fixation light source 140. In this embodiment, the fixation light source 140 can be an LCD screen or an equivalent, and the fixation light 145 can be a bright spot displayed on the dark LCD screen 140.

To facilitate procedures on both eyes, some embodiments may include two fixation light sources 140, one on each side of the objective 112.

In some implementations, the image processor 120 may display the processed image e.g. for informing the medical technician or surgeon. In other implementations at least a portion of the image processed by the image processor 120 may not be displayed by the imaging system 100, only provided in electronic format to the image processor 120 by the imaging device 110.

FIGS. 8A-B illustrate the case when the eye's misalignment is purely angular, as was discussed in relation to FIG. 3B. As before, the optical axis $9i$ of the imaged eye $1i$ may be rotated by the Euler angles $(\theta,\phi)$ relative to the optical axis 28 of the imaging system 100. Correspondingly, the optical axis $9c$ of the control eye $1c$ may be rotated approximately by the same Euler angles $(\theta,\phi)$ relative to the axis of the fixation light source 140, along which the fixation light 145 also propagates.

FIGS. 9A-B illustrate an operation of the image processor 120 configured to analyze the angular misalignment of FIGS. 8A-B. First, the image processor 120 can identify the various ophthalmic structures of the imaged eye $1i$, such as the limbus $6i$, by identifying the high-gradient/contrast lines 122 of the image, as described above.

FIG. 9A illustrates that while an aligned limbus $6ia$ would appear as a circle, in the case of angular misalignment the rotated limbus $6ir$ appears elliptical from the viewpoint of the image processor 120. Thus, in operation the image processor 120 will not be successful fitting a fitting circle 124 as a probe function to the high-gradient/contrast line 122.

FIG. 9B illustrates that once the image processor 120 is unsuccessful fitting a fitting circle 124 then it can attempt to fit a fitting ellipse $124'$ to the high-gradient/contrast line $122'$ to identify the rotated limbus $6ir$ or the rotated pupil $4ir$. The aspect ratio a/c, i.e. the ratio of the length of the minor and major axes of the fitting ellipse $124'$, can be used to determine the Euler angles $(\theta,\phi)$ of angular misalignment of the imaged eye $1i$.

FIG. 8B illustrates that once the image processor 120 was successful determining the Euler angles $(\theta,\phi)$ of the angular misalignment from the aspect ratio a/c of the fitting ellipse $124'$ fitted to the high-gradient/contrast line $122'$, it can compute the misalignment reduction vector $144fa$ with which the fixation light 145 should be moved on the fixation light source 140. This misalignment reduction vector $144fa$ can be constructed so that if the control eye $1c$ follows the fixation light 145 adjusted by the angular misalignment reduction vector $14fa$, as indicated by the solid black arrow, the angular misalignment can be reduced, or possibly even eliminated. Here the f label of the misalignment reduction vector $144fa$ indicates that the misalignment reduction system 130 is of the fixation light 140 type, and the a label refers to an angular misalignment.

Figures 10A, 10B:
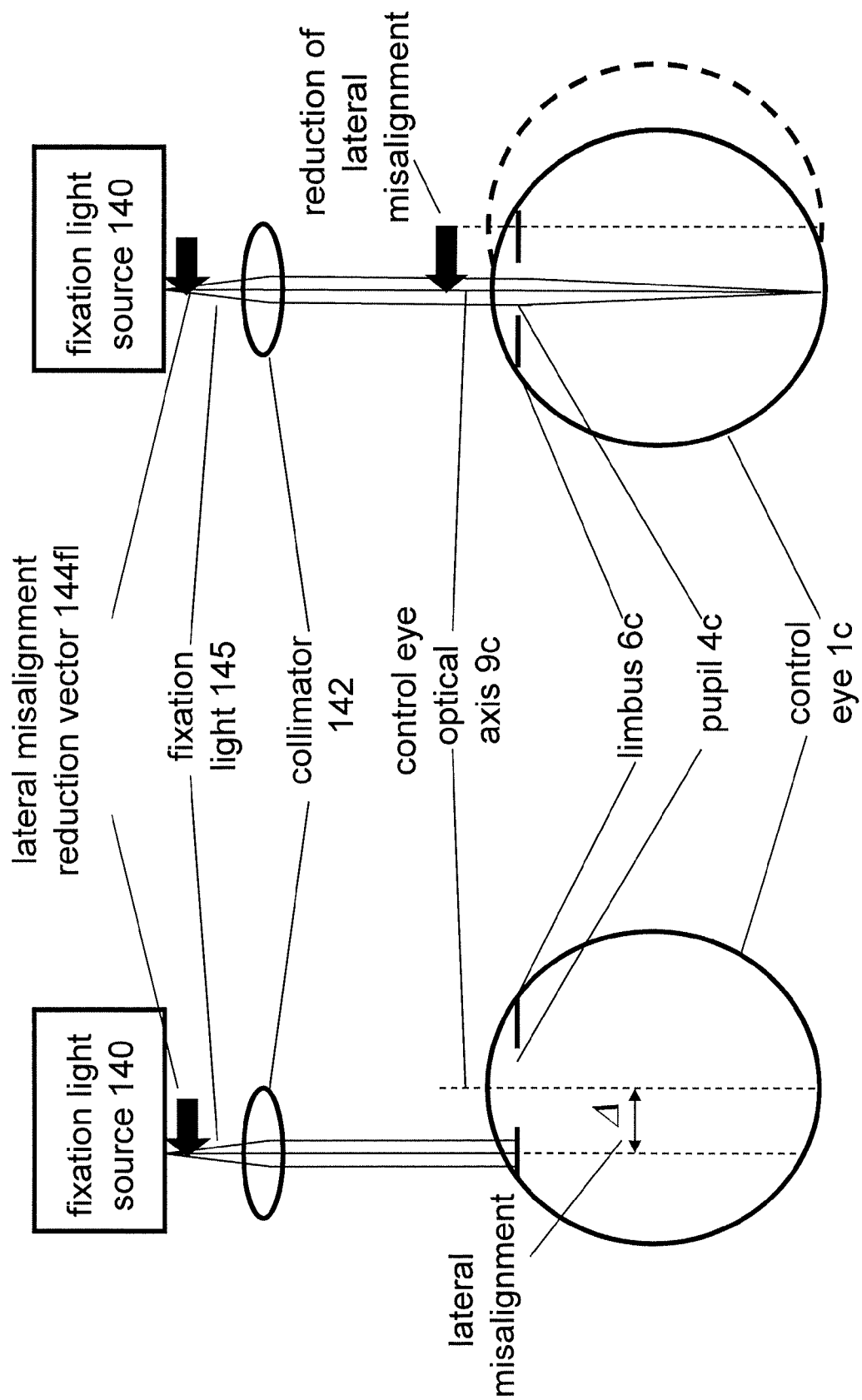
FIGS. 10A-B illustrate a collimated fixation light system.

FIGS. 10A-B illustrate a case of a lateral misalignment $\Delta$. The fixation light sources 140 can include a collimator 142 that can be configured to generate a fixation light 145 to guide the patient to reduce the lateral misalignment $\Delta$ efficiently. The collimator 142 can generate a fixation light 145 with essentially parallel rays, as if it had been generated by a light source at infinity. Thus, the patient 8 can see this collimated fixation light 145 only if he/she looks up straight along the line of the fixation light 145. Therefore, in systems where the collimated fixation light 145 is projected along the optical axis 28 of the system, when the patient manages to adjust the imaged eye to see the collimated fixation light 145, the optical axis $9i$ of the imaged eye is parallel to the system optical axis 28.

In operation, the image processor 120 can determine a lateral misalignment $\Delta$ of the imaged eye from the analysis of the image of the imaged eye $1i$, and compute a corresponding misalignment reduction vector $144fl$, the label l referring to the lateral misalignment in this fixation light system, referred to by the label f. The image processor 120 then can generate a fixation light control signal representing the calculated misalignment reduction vector $144fl$ to be sent to the fixation light source 140. Upon receiving the fixation light control signal, the fixation light source 140 can move or adjust the collimated fixation light 145 with the misalignment reduction vector $144fl$, shown by the solid arrow. The patient 8 can be instructed to move his/her head to find the adjusted collimated fixation light 145. In order to actually see the collimated fixation light 145, the patient 8 will have to move his/her head laterally until the lateral misalignment $\Delta$ is essentially eliminated.

Figure 11:
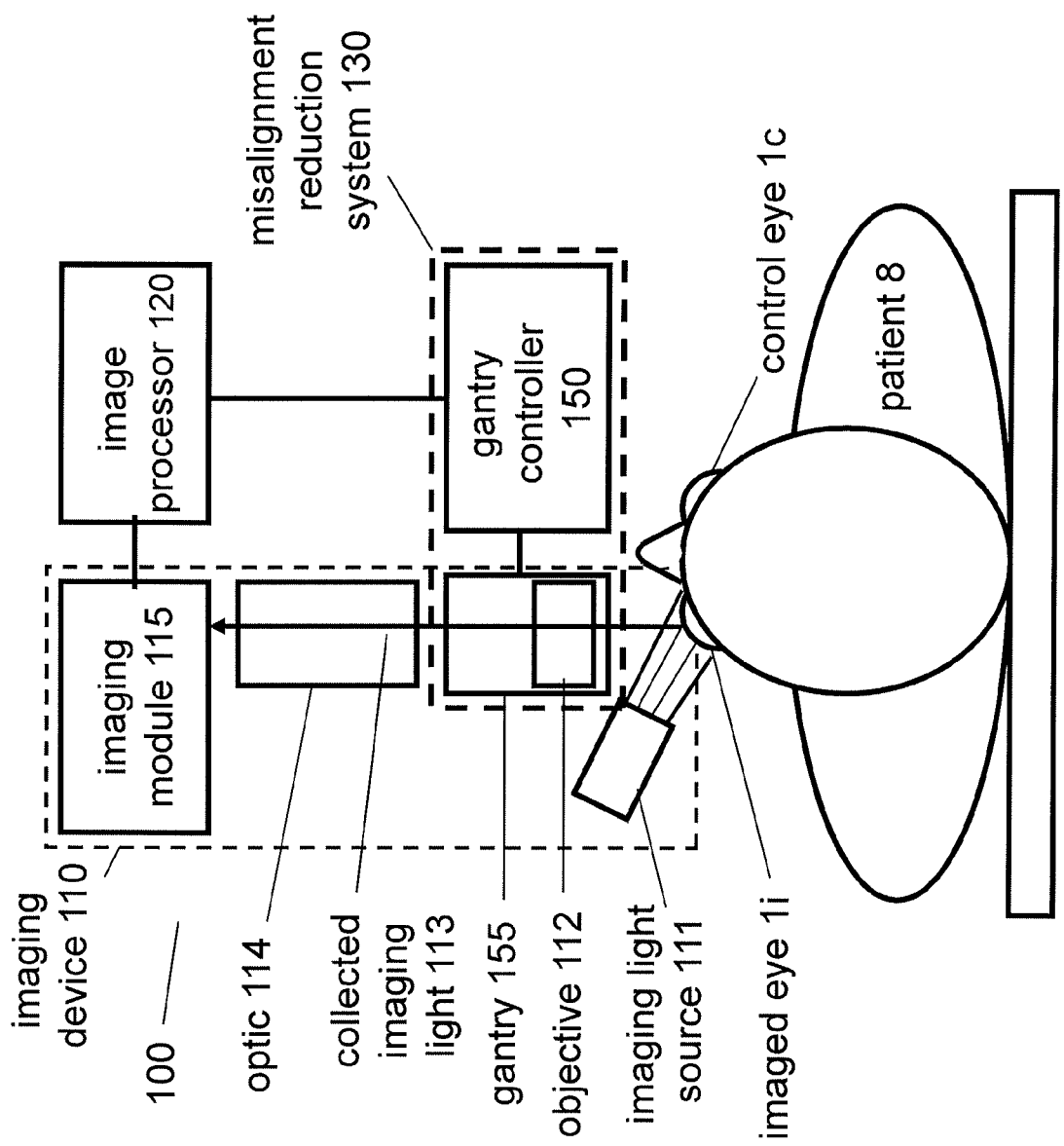
FIG. 11 illustrates a misalignment reduction system with a gantry.

FIG. 11 illustrates an implementation of the misalignment-reduction system 130 that includes a gantry controller 150, configured to receive the fixation light control signal from the image processor 120 and to move a gantry 155 accordingly, wherein the gantry 155 is configured to move a movable portion of the imaging device 110. A motor or actuator, moving the gantry 155 can be part of either the gantry controller 150 or the gantry 155. The movable portion of the imaging device 110 can be the objective 112 or a portion of the optic 114. In this implementation the misalignment-reduction response includes the gantry controller 150 moving the gantry 155 to reduce a lateral misalignment. In some implementations the gantry 155 can be part of the ophthalmic imaging device 110.

Figures 12A, 12B:
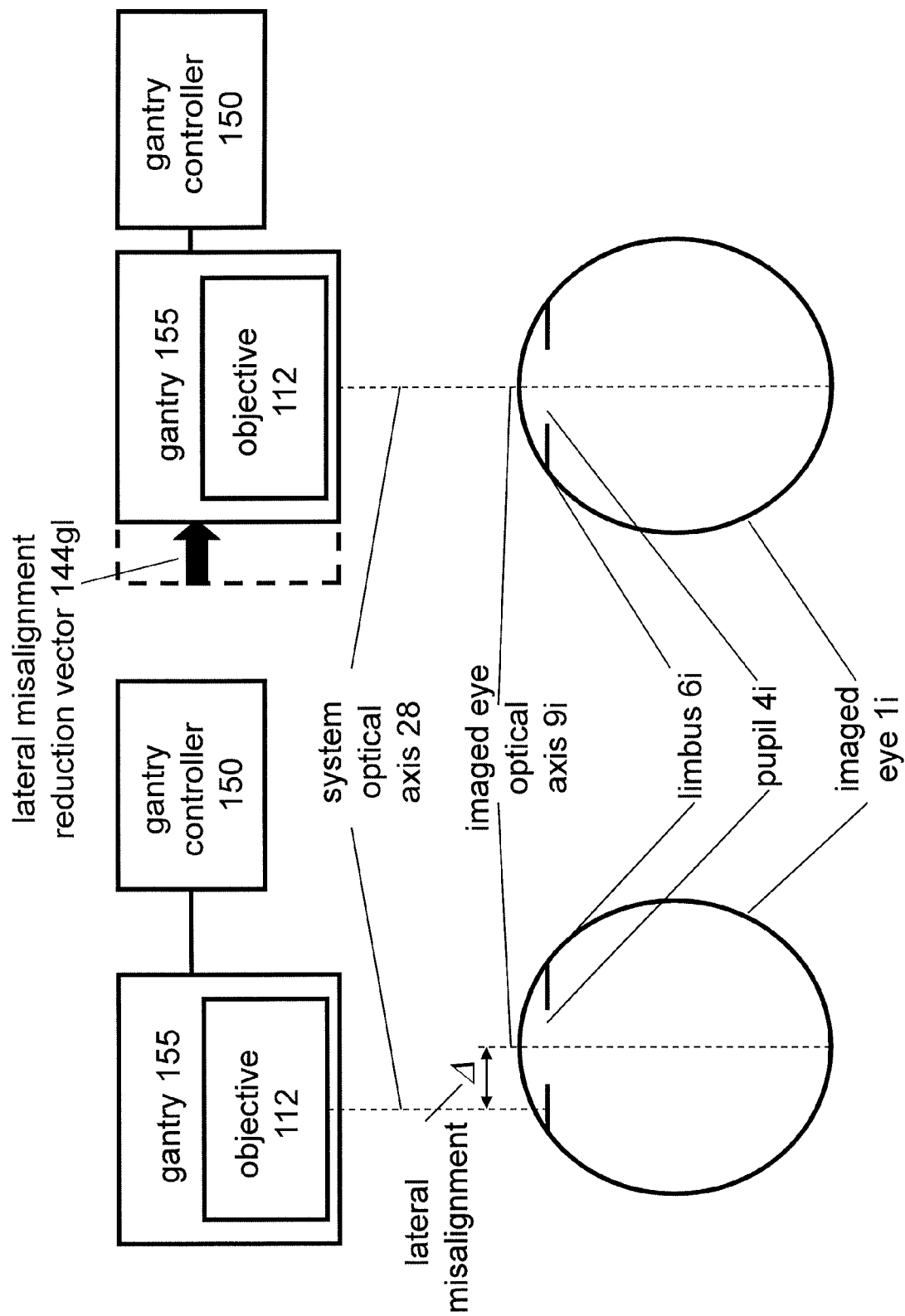
FIGS. 12A-B illustrate an operation of the gantry system.

FIGS. 12A-B illustrate an operation of the gantry-based system of FIG. 11. Often it is the case that the angular misalignment of the imaged eye 1$i$ is minimal, thus the primary purpose of the adjustment process is to reduce the lateral misalignment of the optical axis 9$i$ relative to the optical axis 28 of the imaging device 110. This lateral misalignment, or displacement can be characterized by the misalignment vector 143 ($\Delta x, \Delta y$), or the magnitude of this misalignment vector 143, $\Delta$, as discussed e.g. in relation to FIG. 3A.

FIG. 12A illustrates that the image processor 120 may analyze the image of the imaged eye 1$i$, determine the misalignment vector ($\Delta x, \Delta y$), then determine the corresponding misalignment reduction vector 144$gl$, and output a control signal to the gantry controller 150 representing the misalignment reduction vector 144$gl$. Here the label g refers to the gantry type misalignment reduction system 130.

Some aspects of these gantry-based systems differ from those of the fixation light systems of FIGS. 6-10. In these gantry-based systems, the patient is not necessarily asked to move the imaged eye 1$i$, as the gantry 155 is configured to move the movable portion of the imaging device 110 to reduce or eliminate the lateral misalignment.

FIG. 12B illustrates that the gantry controller 150 can, in response to the control signal, move the gantry 155 with the lateral misalignment reduction vector 144$gl$ to eliminate the lateral misalignment $\Delta$ and align the optical axis 9$i$ of the imaged eye with the optical axis 28 of the imaging device 110.

In practice, an ophthalmic surgeon often faces a combination of the above angular and lateral misalignments. Advanced single-component implementations of the misalignment-reduction system 130 may be able to reduce or eliminate both of these misalignments, as described next.

For example, in a misalignment-reduction system 130 with a fixation light source 140 component only, in a first phase the image processor 120 may follow the method of FIG. 9 to compute the angular misalignment of the imaged eye 1$i$. However, the elliptic distortion of the limbus 6$i$ can be caused both by the angular misalignment and by the lateral misalignment and these two effects need to be separated.

In an implementation the image processor 120 can project the fixation light 145 at a suitable first location and the patient can be instructed to focus on this once-adjusted fixation light 145. From measuring the ellipticity of the limbus 6$i$, the knowledge of first location and the location of the eye on the imaging interface 115, the image processor 120 can determine the lateral and angular misalignments. Based on the determined lateral misalignment, the patient can be instructed to move the imaged eye 1$i$ to the center of the imaging device 110. This process may be performed iteratively to reach sufficient precision. Sometimes the fixation light 145 can be readjusted and the ellipticity re-measured to assist the process.

After the eye is centered with sufficient precision, the image processor 120 may adjust the fixation light 145 for a second time, typically to a second location corresponding to the center of the imaging device 110. The patient 8 focusing on this twice adjusted fixation light 145 can eliminate the angular misalignment as well.

The apparent ellipticity of the limbus 6$i$ may have a third cause as well besides the two types of misalignments: often the limbus 6$i$ itself is not entirely circular. In some implementations, the image processor 120 may need to perform an advanced image processing algorithm to separate the three causes of the ellipticity. The advanced image processing may include tracking suitably chosen merit functions or the analysis of optical distortions of the image. An example of the merit function can be the area of the fitted ellipse.

Similarly, the single-component gantry-based misalignment-reduction system 130 may be able to correct both types of misalignments in separate phases as well.

If the above described two-phase methods only reduced the two misalignments but did not eliminate them, the two phases can be repeated iteratively to substantially eliminate the two types of misalignments. A large variety of optimization and other search algorithms can be used to facilitate such iterative approaches.

Figure 13:
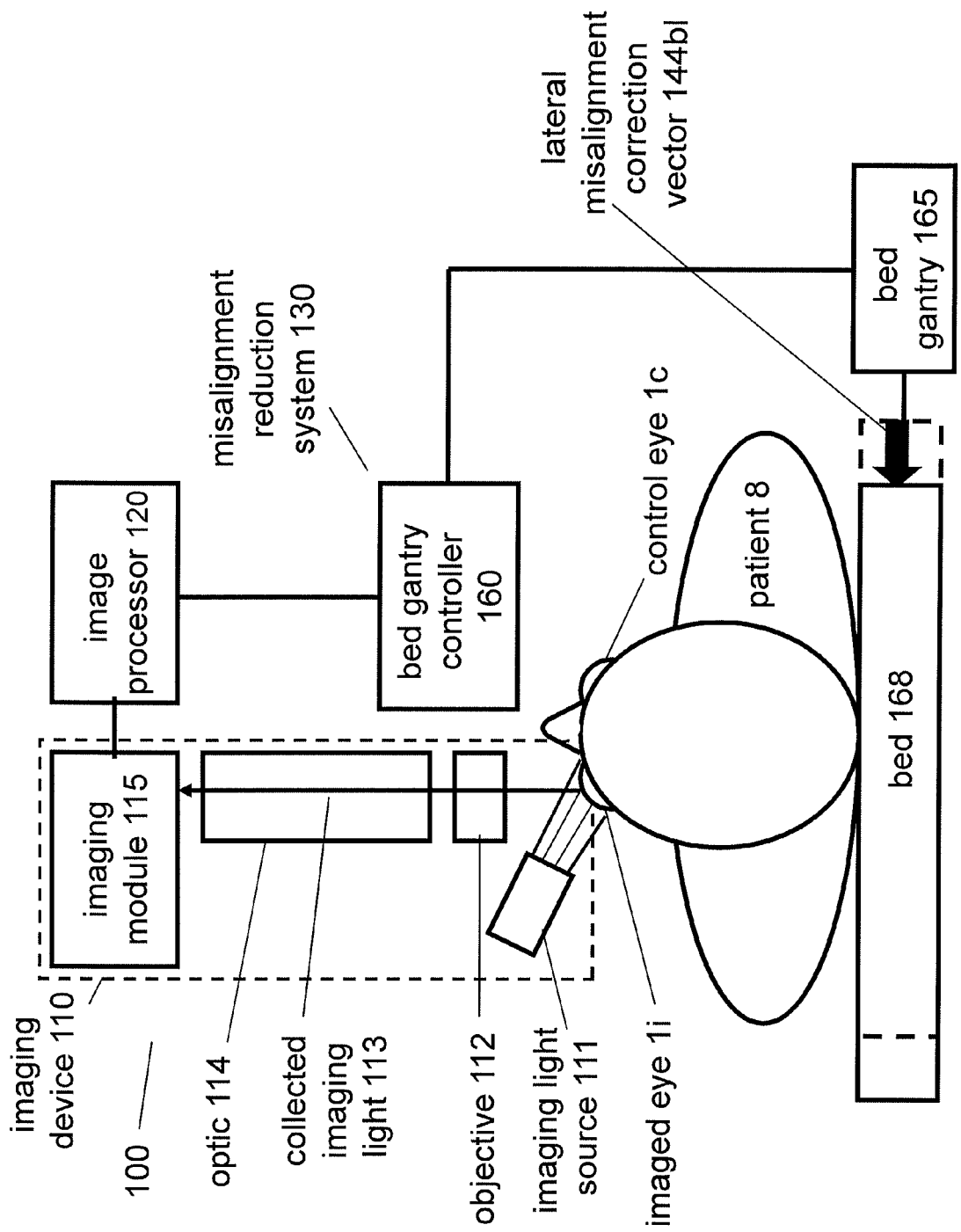
FIG. 13 illustrates a bed gantry system.

FIG. 13 illustrates an implementation of the misalignment-reduction system 130 that includes a movable patient support, such as a bed 168, moved by a support/bed gantry 165 that is controlled and moved by a bed gantry controller 160. Upon receiving the control signal from the image processor 120, the gantry controller 160 can move the support/bed gantry 165 by a lateral misalignment reduction vector 144$bl$, which in turn moves the patient support/bed 168. Here the b label stands for the bed 168.

Aspects of this implementation include that the relative position of the optical elements in the imaging device 110 are not changed during regular operations, thus a high level of alignment and precision of the optics can be maintained. At the same time, the weight and physical extent of the patient support 168 is much greater than that of the objective 112, thus the high precision adjustment of the patient support 168 has its own challenges.

Figure 14:
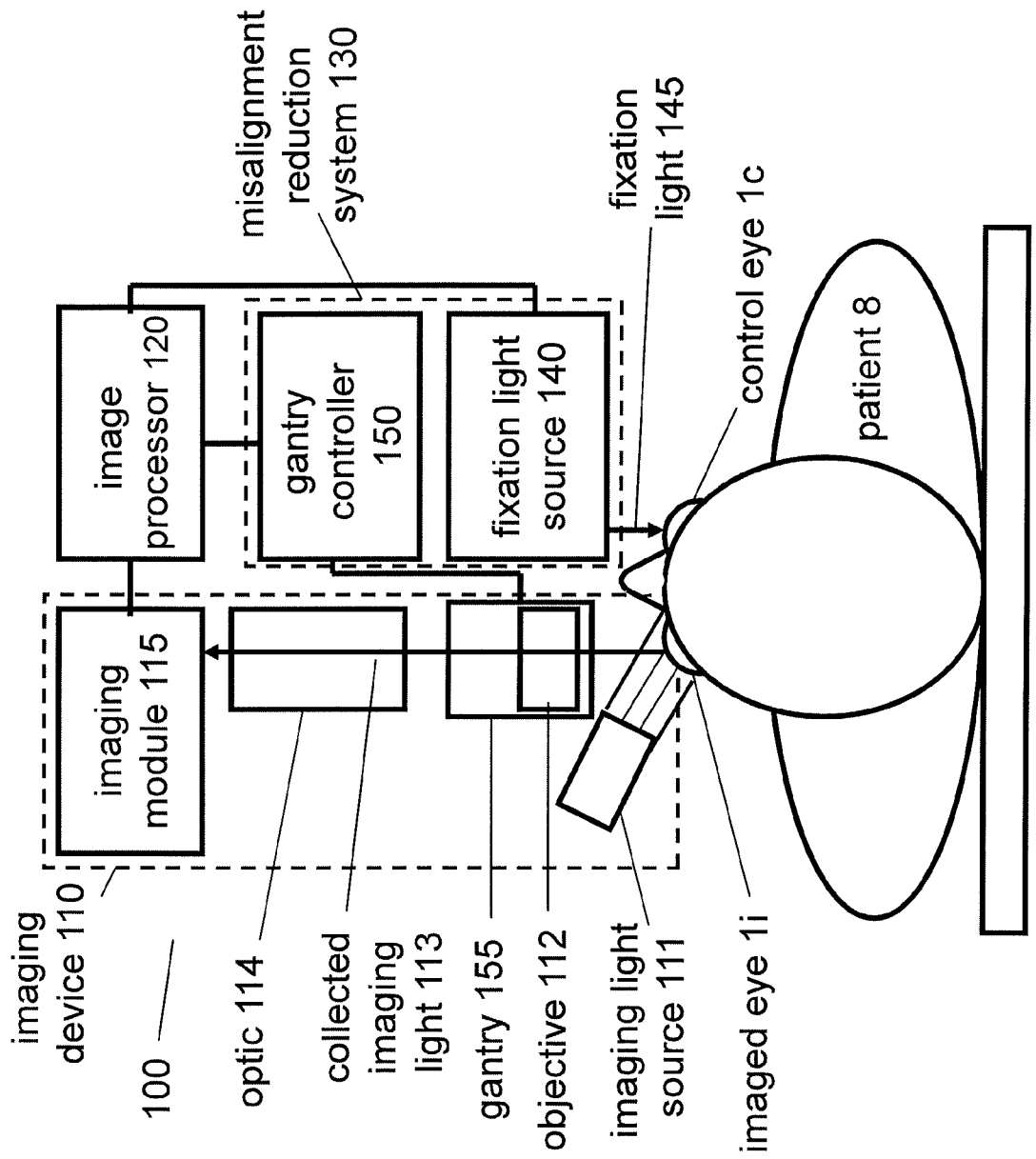
FIG. 14 illustrates a system combining a fixation light and a gantry.

FIG. 14 illustrates that some implementations of the misalignment reduction system 130 may contain both a fixation light system 140-145 and a gantry system 150-155. Such an integrated misalignment reduction system 130 may allow the surgeon to reduce and eliminate both types of misalignments in an efficient manner.

Figure 15A:
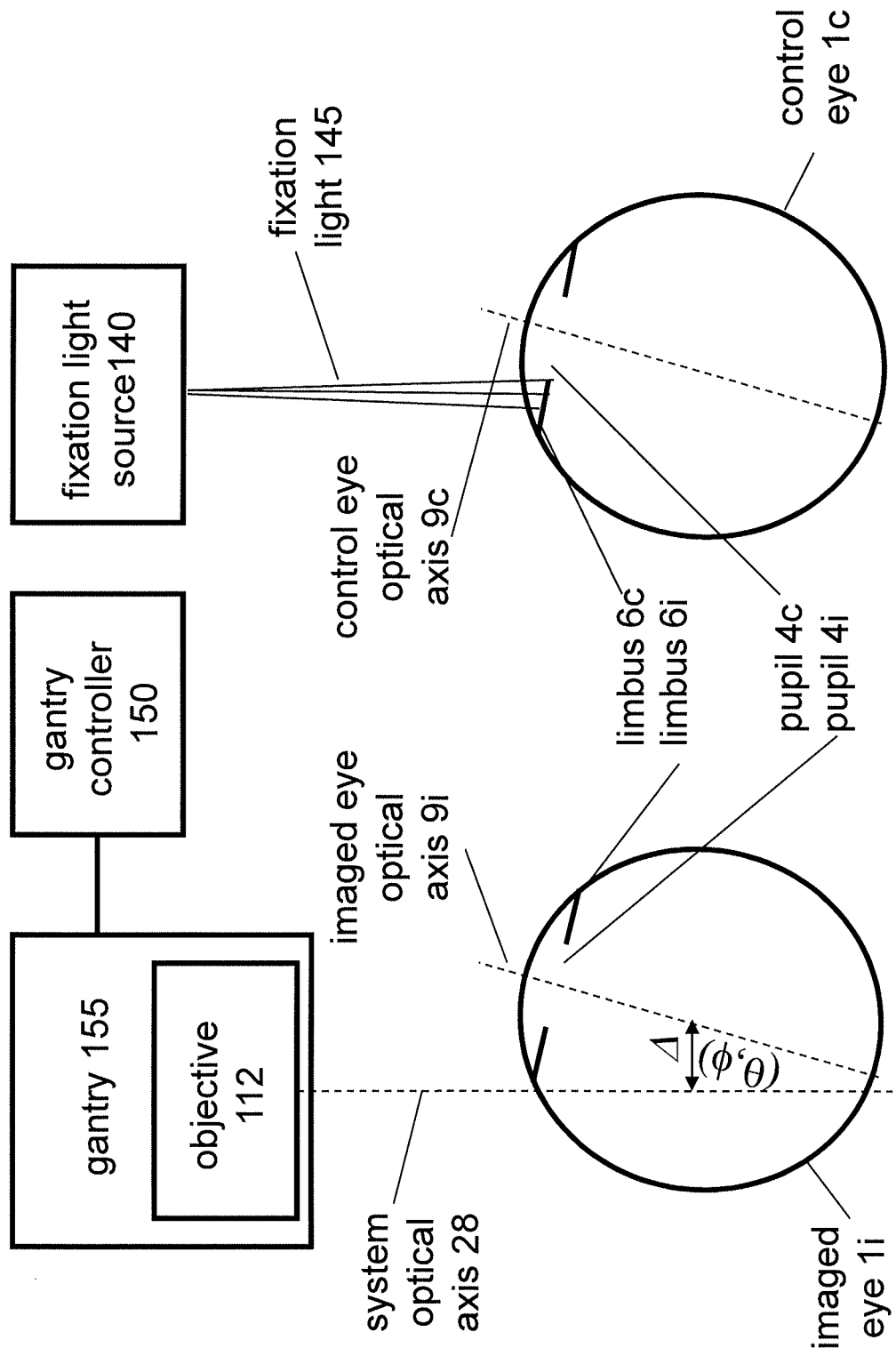
FIGS. 15A-B illustrate an operation of the fixation light-and-gantry system.
Figure 15B:
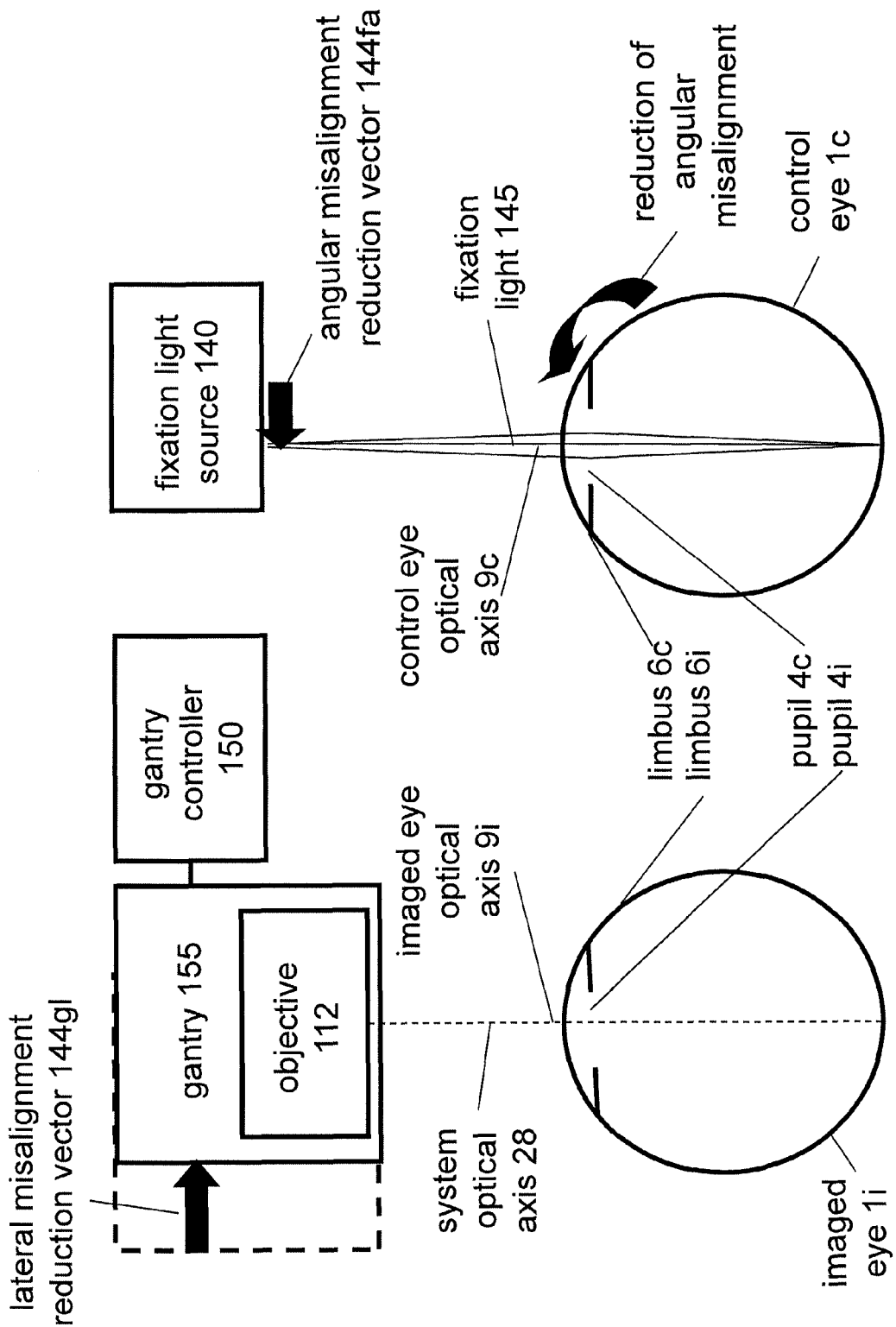

FIGS. 15A-B illustrate that in some embodiments, the image processor 120 may be able to determine the lateral and angular misalignments by the above described methods and direct the fixation light source 140 and the gantry controller 150 to reduce the misalignments.

FIG. 15A illustrates a typical situation, where the imaged eye has both a lateral misalignment $\Delta$ or ($\Delta x, \Delta y$) and an angular misalignment ($\theta, \phi$). To handle such situations, the image processor 120 can be configured to analyze the image and compute a lateral misalignment reduction vector 144$l$ and an angular misalignment reduction vector 144$a$. As before, there are a large number of different measures of the misalignment, which can be expressed in terms of angular, linear, percentage and other variables. The term "misalignment vector" can refer to any of these variables, measures and their combinations.

FIG. 15B illustrates that the patient can be instructed to follow the fixation light 145 that is adjusted by the angular misalignment reduction vector 144$fa$ to eliminate the angular misalignment. Then the gantry controller 150 can adjust the gantry 155 with the lateral misalignment reduction vector 144gl to eliminate the lateral misalignment. Integrated embodiments with such a gantry 155 can reduce the lateral misalignment efficiently and with high precision as they do not rely on the patient moving the imaged eye laterally.

The two phases of alignment reduction can be performed in the opposite order or in alternating repeated phases. Referring to FIG. 13, the gantry can also be the support gantry 165, moving the patient support 168 instead of the objective 112 or the movable portion of the optic 114.

Figures 16A, 16B:
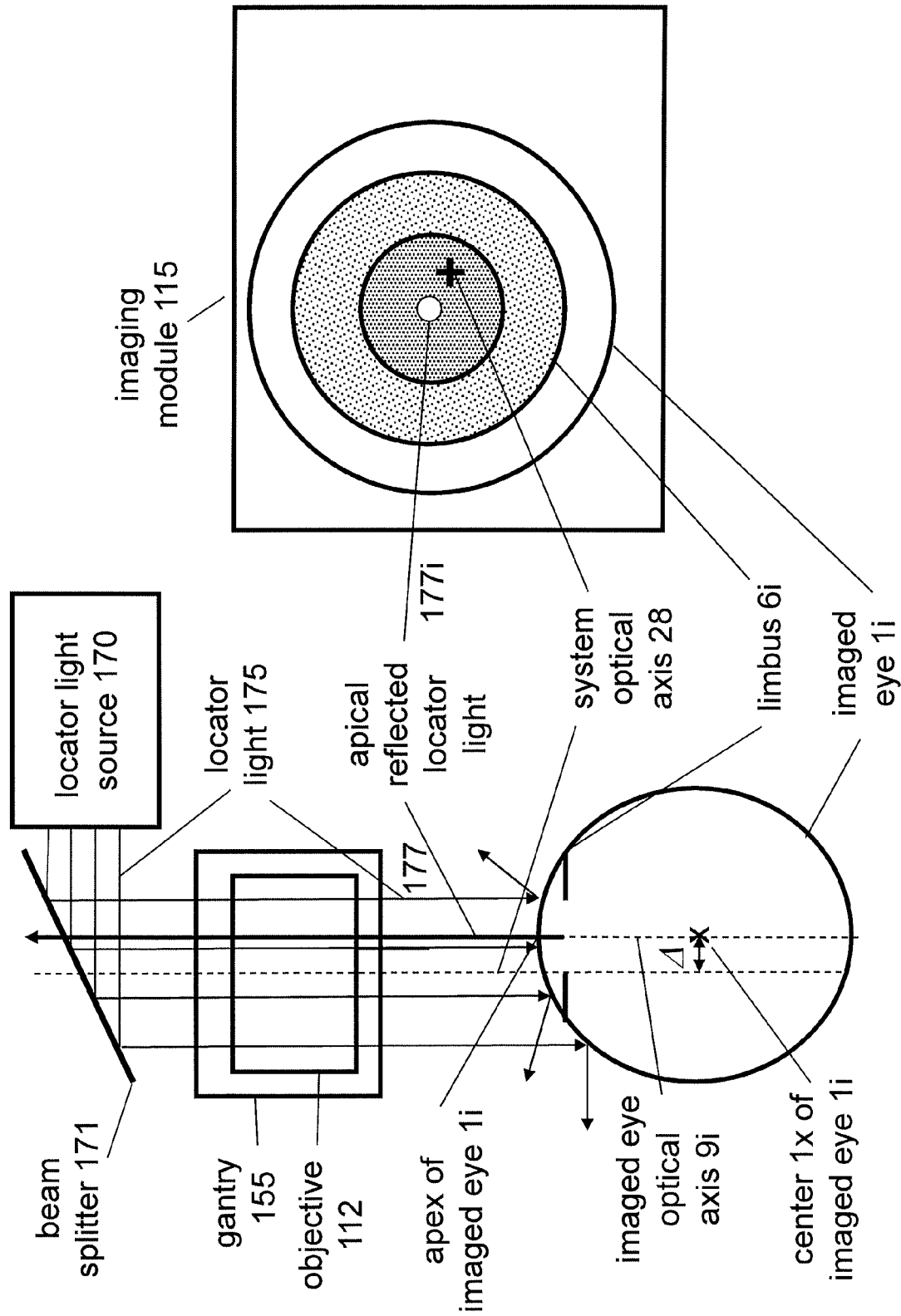
FIGS. 16A-B illustrate a system with a locator light.

FIGS. 16A-B illustrate that in some integrated systems the image processor 120 may be configured to determine the angular and the lateral misalignment by processing the image and an additional misalignment information.

The misalignment information can be originated by a locator light source 170. The locator light source 170 can generate a locator light 175 which can be coupled into the main optical pathway by a beam splitter 171. The optic 114 and in particular the objective 112 can guide or project the locator light 175 onto the imaged eye 1i.

If the imaged eye 1i can be approximated by a reflecting sphere, or at least a portion of a reflecting sphere, then standard geometric considerations reveal that the portion of the locator light 175 that reflects back into the objective 112 parallel to the optical axis 28 is the one that is reflected from the apex of the spherical eye 1. This reflected light will be referred to as an apical reflected locator light 177. The other rays are shown to reflect away from the system optical axis 28.

FIG. 16B illustrates that an image 177i of the apical reflected locator light 177 can be detected by the image processor 120 in the overall image generated by the imaging device 110 on the imaging module 115, as shown by the white spot.

For a spherical imaged eye 1i having a lateral misalignment Δ relative to the system optical axis 28, the white spot image of the apical reflected locator light 177i does not coincide with the system optical axis, indicated by the solid cross. It is noted though that the relative locations of the white spot and the black cross are independent from a possible angular misalignment of the image eye. Thus, for spherical eyes the vector connecting the imaged apical reflected locator light 177i with the cross-mark of the system optical axis 28 can provide the additional alignment information for the image processor 120 that enables it to determine the lateral misalignment independently from the angular misalignment.

FIGS. 17A-B illustrate that the imaged eye is more appropriately modeled as a primary sphere with a protruding secondary sphere, corresponding to the cornea 2. Some implementations of the image processor 120 can be configured to determine the misalignment information by analyzing the imaged apical reflected locator light 177i on the basis of this more realistic model. For this analysis, the image processor 120 can use one or more fitting parameters, or the results of pre-procedure imaging measurements.

FIGS. 17A-B illustrate a generic case with simultaneous angular misalignment (θ,φ) and lateral misalignment Δ. If the imaged eye 1i has only the lateral misalignment Δ, then the image spot of the apical reflected locator light 177i coincides with the center of the limbus 6ic, indicated by a solid x in FIG. 17B. This limbus center 6ic is not directly detected, but can be computed e.g. by fitting the fitting circle 124 to the image of the limbus 6i.

Therefore, the vector or distance connecting the image spot of the apical reflected locator light 177i and the limbus center 6ic is an example of a dominantly or purely angular misalignment information that can be used by the image processor 120 to generate a misalignment reduction vector 144fa for the fixation light source 140 to correct this angular misalignment.

On the other hand, determining the lateral displacement Δ, e.g. between the system optical axis 28 and the center 1x of the imaged eye 1i, may be more challenging when the complex shape of the eye is taken into account than the procedure in FIGS. 16A-B. Therefore, in a first phase, an operator of the system 100 may adjust the fixation light 145 and instruct the patient to focus on the adjusted fixation light 145 until the limbus center 6ic and the image spot of the apical reflected locator light 177i overlap or coincide, thus eliminating the angular misalignment and aligning the system optical axis 28 with the imaged eye's optical axis 9i.

In a subsequent second phase, the distance or vector between the system optical axis 28, indicated by the solid cross, and the overlapping image spot of the apical reflected locator light 177i and the limbus center 6ic (solid x) can provide a lateral misalignment information. The image processor 120 may compute the lateral misalignment reduction vector 144gl using this lateral misalignment information and send a corresponding control signal to the gantry controller 150. In response, the gantry controller 150 can adjust the gantry 155 with the lateral misalignment reduction vector 144gl.

Numerous equivalent implementations of the above principles can be practiced as well, for example performing the first and second phases in repeated iterative steps or in reverse order.

Figure 18:
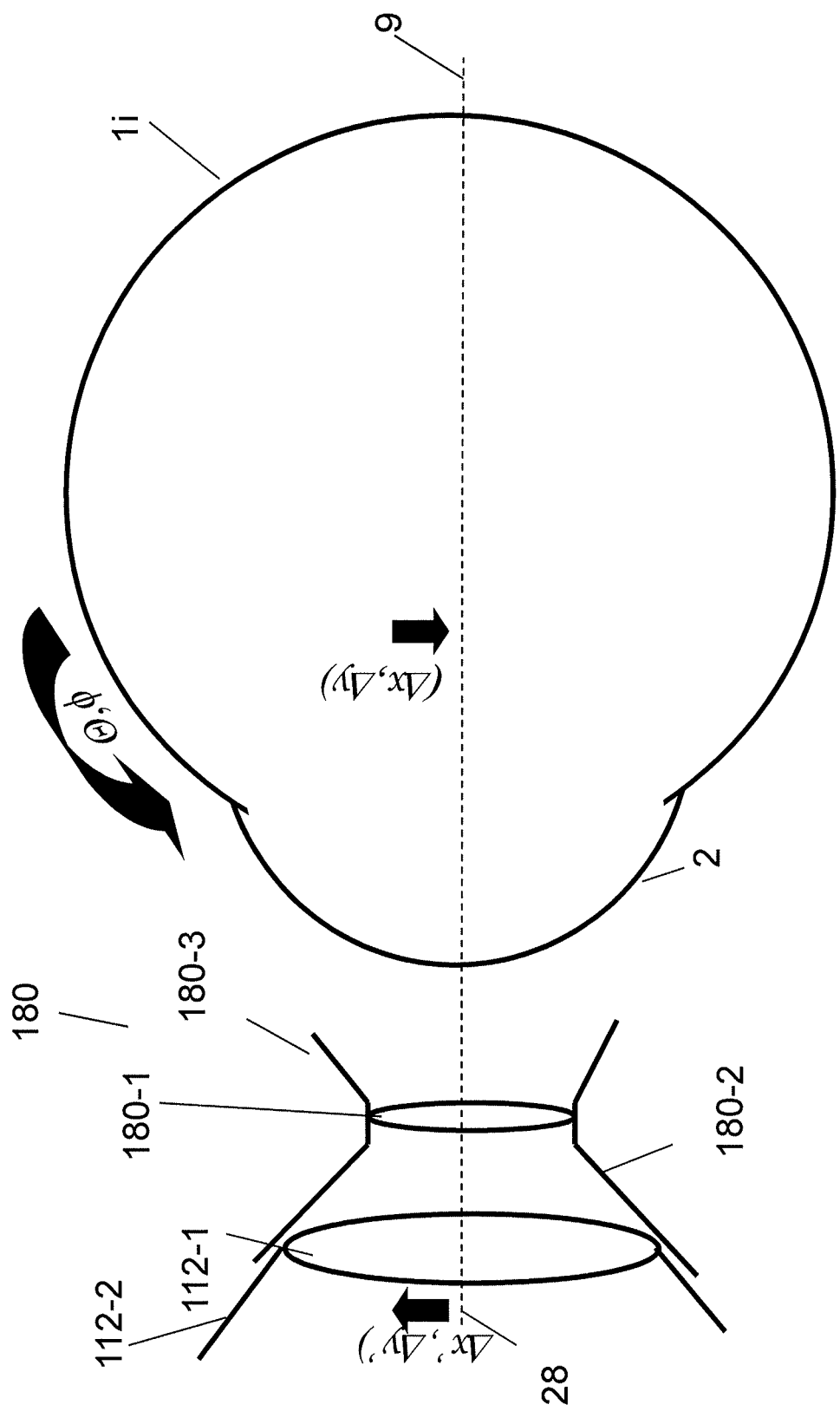
FIG. 18 illustrates the reduction of the lateral and angular misalignment.

FIG. 18 illustrates that some implementations of the misalignment reduction system 130 are configured to reduce or even eliminate both the angular and lateral misalignments by the above operations. As shown, the lateral misalignment can be reduced by the movement of the imaged eye 1i alone, or by the complementary lateral movement (Δx,Δy) of the imaged eye 1i and (Δx',Δy') of the imaging device 110.

Once both types of misalignments have been reduced or eliminated by the misalignment-reduction system 130, the operator of the ophthalmic system 100 may lower a patient interface 180, configured to dock to the imaged eye 1i of the patient. This patient interface 180 can immobilize the imaged eye 1i to keep it fixed for subsequent procedures. These procedures may include diagnostic procedures, imaging procedures and ophthalmic surgical procedures.

In detail, the objective 112 of the ophthalmic system 100 can include a distal objective lens 112-1, contained in an objective housing 112-2. The patient interface 180 can include an interface lens, contact lens, sometimes also called applanation plate 180-1, contained in an interface housing 180-2. The patient interface 180 may be attached to the objective 112 or to the distal end of the imaging system 110. In other embodiments, part of the patient interface 180 can be attachable to the eye and the other part to the distal end of the imaging system 110. The patient interface 180 can be attachable to the eye with a suction ring or vacuum skirt 180-3.

In these architectures, the patient interface 180 can be docked with the imaged eye 1i after the alignment of the imaged eye 1i with the imaging device 110 has been completed. In other embodiments, the patient interface 180 can be docked with the imaged eye 1i in an iterative manner. First, the imaged eye 1i can be brought into alignment with the imaging device 110. Second, the patient interface can be lowered onto the imaged eye 1i to make contact, but still allowing the imaged eye 1i some movement. But since during the first phase the imaged eye 1i may have moved, or the image processor 120 may not have determined the alignment perfectly, in a third phase the alignment procedure can be repeated and one or more new misalignment reduction vectors can be computed by the image processor 120. Fourth, the imaged eye 1*i* can be realigned using the newly computed misalignment reduction vector(s). These partial or stepwise phases can be followed by the full strength docking of the patient interface 180 onto the imaged eye 1*i*, preventing further relative movement of the imaging device 110 and the imaged eye 1*i*.

Figures 19A, 19B:
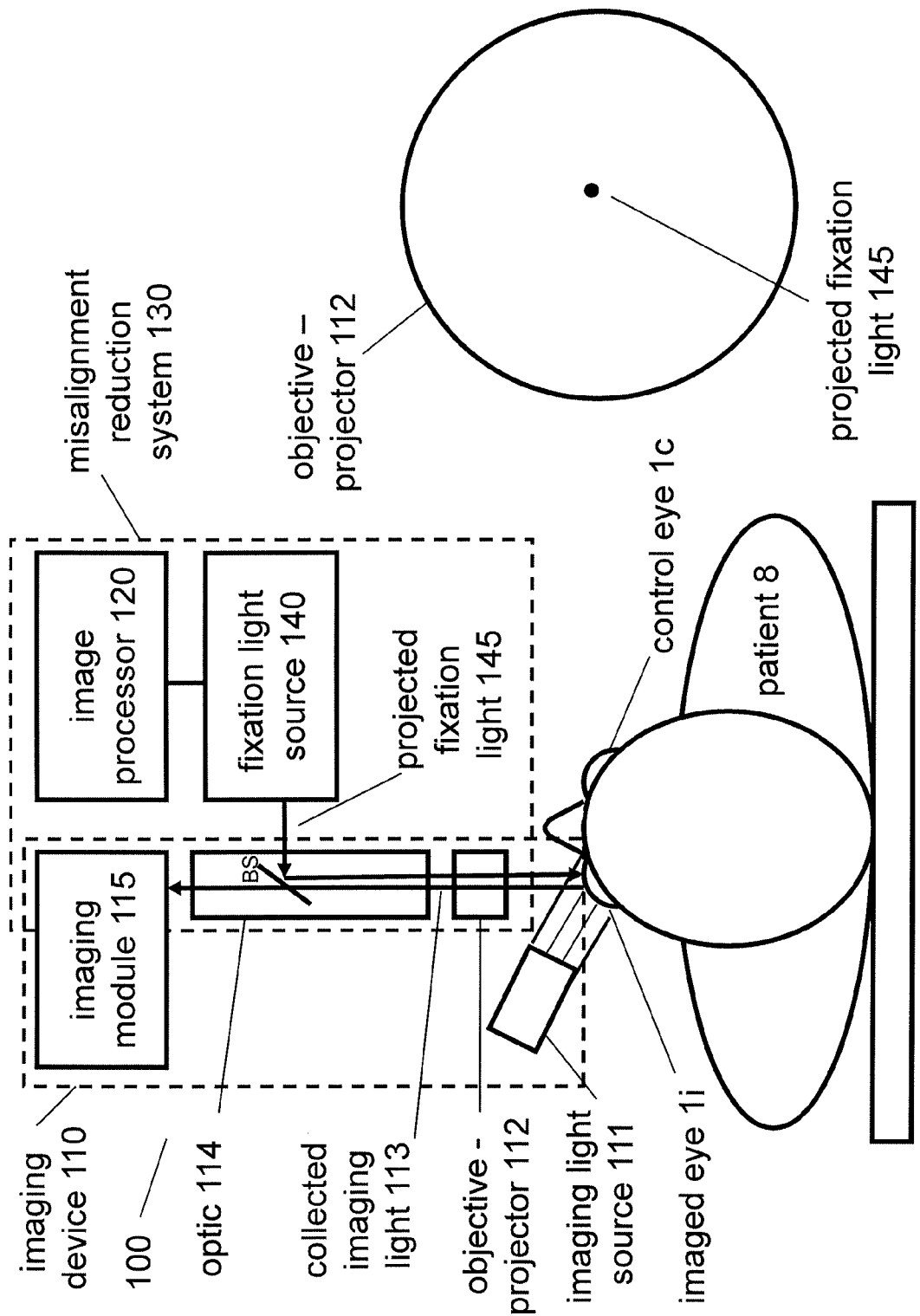
FIGS. 19A-B illustrate a fixation light system, projecting the fixation light into the imaged eye of the patient.

FIGS. 19A-B illustrate that in some embodiments of the ophthalmic system 100, the fixation light source 140 can project the fixation light 145 not onto the control eye 1*c*, but into the main optical pathway of the imaging device 110 with a beam splitter BS, so that the fixation light 145 is projected onto the imaged eye 1*i* instead.

FIG. 19B illustrates the appearance of the embodiment 100 for the patient: the fixation light 145 appearing in the objective 112 itself, instead of a separate fixation light source 140. In these embodiments, the patient may be instructed to follow the fixation light by the imaged eye 1*i* instead of the control eye 1*c*. The other elements of these embodiments 100 as well as the principles of their operation can be analogous or equivalent to the above described systems.

FIGS. 20A-B illustrate variations of the embodiment 100 of FIGS. 19A-B. In these embodiments, the locator light 175 can be used as a second fixation light. For example, the locator/second fixation light 175 can be focused to a second focal point 176, located at a z-coordinate z2 different from the z-coordinate z1 of the first focal point 146 of the first fixation light 145. Here the z-coordinates of the fixation lights can be measured from a z0 reference level along the optical pathway. The z-coordinate z1 of the first focal point 146 of the first fixation light 145 need not be at the distal end of the objective 112 as shown. The patient 8 can be instructed to move and rotate the imaged eye 1*i* to align the first fixation light 145 and the second fixation light 175, in effect to align the first focal point 146 and the second focal point 176. If the first and second focal points 146 and 176 both lie on the system optical axis 28, this procedure guides the patient to align the imaged eye optical axis 9*i* with the system optical axis 28. This functionality can be implemented in several different ways.

In some cases the first focal point 146 can be fixed to lie on the system optical axis 28. In these implementations, (i) the image processor 120 can identify the lateral and angular misalignments of the imaged eye 1*i* by processing the image of the eye 1*i*; (ii) the image processor 120 can present or project the second fixation light 175 with a suitably located initial focal point 176, and (iii) the image processor 120 can move or adjust the second fixation light 175 towards the system optical axis 28 to guide the patient 8 to align the imaged eye optical axis 9*i* with the system optical axis 28. In FIG. 20A the adjustability of the second focal point 176 is indicated with a solid arrow.

In another implementation, the second fixation light 175 and its focal point 176 can be fixed on the system optical axis 28 and the first focal point 146 can be adjusted by the image processor 120 to guide the patient 8 to align the imaged eye optical axis 9*i* with the system optical axis 28. In FIG. 20A the adjustability of the first fixation light 145 and its focal point 146 is indicated with a solid arrow.

FIG. 20A illustrates that in yet other implementations, both the first focal point 146 and the second focal point 176 can be adjustable, indicated by the two solid arrows. In these implementations the image processor 120 can carry out more complex or optimized guidance protocols to guide the patient 8 to align the imaged eye optical axis 9*i* with the system optical axis 28.

FIG. 20B illustrates yet other embodiments based on the above design principles. In the collimator implementation of FIGS. 10A-B the ophthalmic system 100 projects a collimated fixation light 145 to the eye. However, since the collimator 142 makes the rays of the fixation light 145 essentially parallel, the patient may not be able to see the collimated fixation light 145 from a typical misaligned initial position. In such systems, the patient 8 may not be able to follow instructions to align the imaged eye with the collimated fixation light 145 and may need assistance.

Some embodiments may assist the alignment process in these collimator implementations with providing the locator light 175, focused at the second focal point 176. Since the locator light 175 is not collimated, the patient 8 is able to see the second focal point 176 even from misaligned positions. In these embodiments, after the patient 8 fixates on the locator light 175, the image processor 120 can subsequently move or adjust the locator light 175 (shown by the solid arrow) to assist the patient to rotate and move the imaged eye until the patient sees the collimated fixation light 145.

FIG. 21 illustrates that some ophthalmic systems 100 can also include a procedure laser 190. The procedure laser 190 can be used to perform an ophthalmic surgical procedure after the high precision alignment and docking made possible by the misalignment reduction system 130. The surgical procedure can include a cataract surgery, a refractive procedure, a retina-related procedure and a wide variety of other ophthalmic procedures.

Some of these ophthalmic systems 100 may also include a secondary imaging system 195. This secondary imaging system 195 can include an optical coherence tomographic (OCT) system. OCT systems, especially the spectrometer based frequency-domain type, are well suited to image three dimensional ophthalmic target regions, as they are capable of acquiring image data from all depth of the target region simultaneously. The beams of the procedure laser 190 and the secondary imaging system 195 can be coupled into the main optical pathway by beam splitters BS1 and BS2, respectively. Such systems may combine the z-directional imaging functionality of the OCT imaging system 195 with the above described image processing-based alignment procedure to achieve alignment both with visible ophthalmic structures as well as with targets inside the eye.

Figure 22:
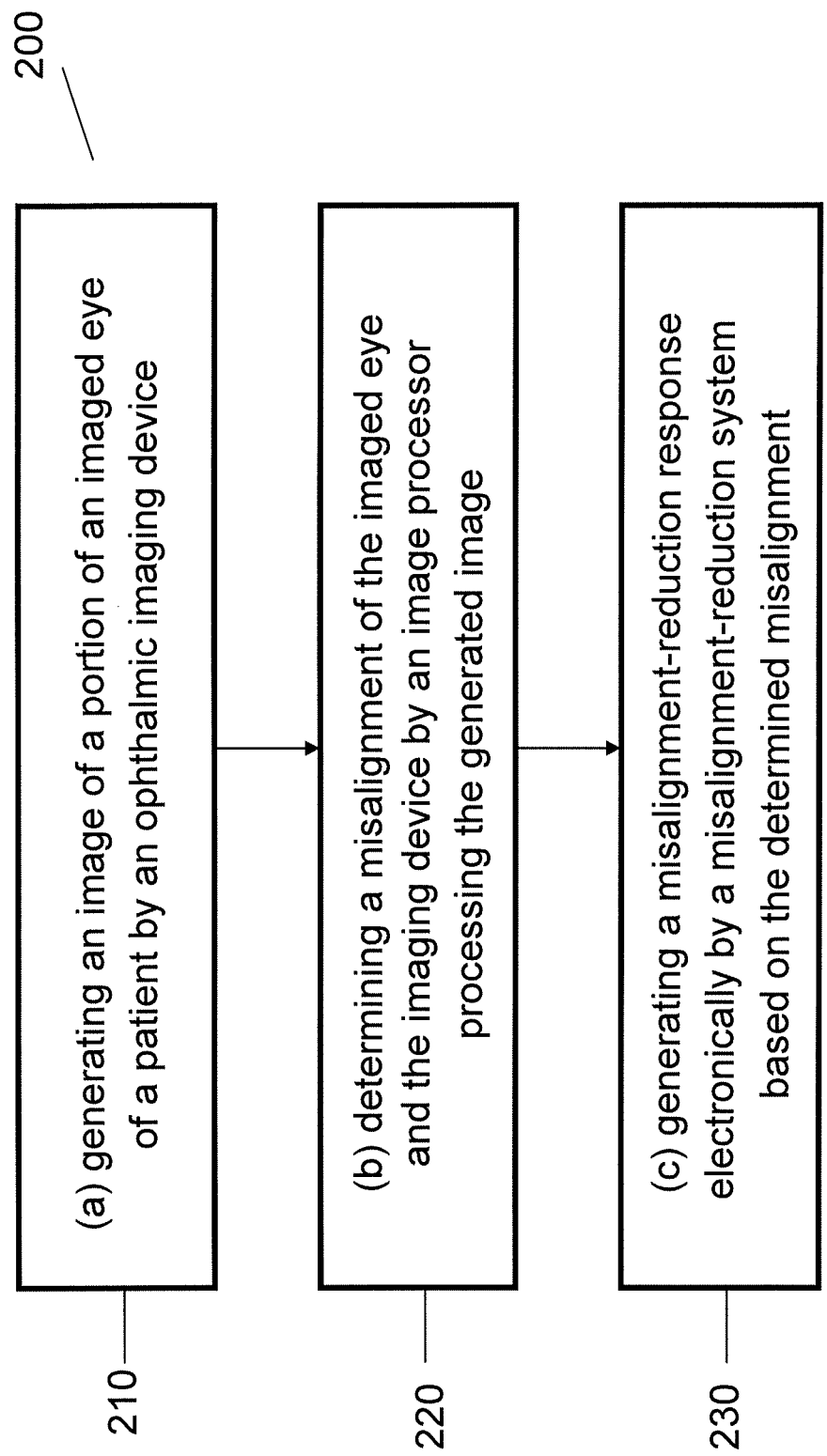
FIG. 22 illustrates a method of operating the ophthalmic system with the misalignment reduction system.

FIG. 22 illustrates an operation of the above described ophthalmic system 100. A method 200 of aligning an eye with the ophthalmic system 100 can include the following phases. (a) A generating of an image 210 that generates an image of a portion of the imaged eye 1*i* of a patient by the ophthalmic imaging device 100. (b) A determining a misalignment 220 that determines the misalignment of the imaged eye 1*i* and the imaging device 110 by an image processor 120 processing the generated image. (c) A generating a misalignment-reduction response 230 that generates a misalignment-reduction response electronically by a misalignment-reduction system based on the determined misalignment.

The generating an image 210 can include generating an image 212 of a portion of the imaged eye 1*i* with the imaging device 110.

The determining the misalignment 220 can include (1) identifying an ophthalmic structure 222 in the image 212. The ophthalmic structure can be the pupil 4, the lens 5, and the limbus 6, among others. The determining 220 can also include (2) determining the misalignment by determining a location of the ophthalmic structure 222 relative to a reference of the imaging device by the image processor 120. The reference of the imaging device can be the objective 112, a patient module, a docking tip, an interface, a contact lens, a pupil, a viewing frame, a reference frame, an internal lens of the ophthalmic system, or a reference pattern 117 generated by the imaging device 110. The misalignment can be a lateral or an angular misalignment, determined by the image processor 120 by analyzing the image using software implementations. Finally, (3) the image processor 120 can generate a control signal according to the determined misalignment and output the generated control signal to the misalignment-reduction system 130.

The generating the misalignment-reduction response 230 can include generating the misalignment-reduction response 230 by the misalignment reduction system 130. In some embodiments, the generating the misalignment-reduction response 230 can include generating the fixation light 145 by the fixation light source 140 according to the misalignment determined by the image processor 120, in response to the control signal from the image processor 120. The fixation light 145 can guide the patient 8 to reduce an angular or a lateral misalignment.

In an implementation, the fixation light source 140 may include a collimator 142 to generate the fixation light 145 to guide the patient 8 to reduce a lateral misalignment. The fixation light 145 can be generated for the non-imaged, or control eye 1c, and the fixation light 145 can be adjusted according to the determined misalignment to assist the patient to reduce the misalignment. In other implementations, the fixation light 145 can be generated for the imaged eye 1i.

The generating the misalignment-reduction response 230 can include the gantry controller 150 moving the gantry 155 of the imaging device 110 to reduce a lateral misalignment. In other embodiments, the gantry controller 150 can move the bed 168, or a combination of the bed 168 and the gantry 155.

The determining the misalignment 220 can include determining an angular and a lateral misalignment by the image processor 120 processing the image and an additional misalignment information. Correspondingly, the generating the misalignment-reduction response 230 can include operating the fixation light system 140 and the gantry controller 150 to reduce the angular and the lateral misalignment.

The determining the misalignment 220 can include (1) projecting the locator light 175 onto the imaged eye 1i by the locator light source 170, (2) locating an image 177i of the apical reflected locator light 177 in the image generated by the imaging device 110, and (3) determining the misalignment information using the located imaged apical reflected locator light 177i.

The determining the misalignment information 220 can include determining an angular misalignment information, related to a distance or vector between the image of the apical reflected locator light 177i and a location of an imaged ophthalmic structure; and determining a lateral misalignment information, related to a distance or vector between the imaged apical reflected locator light 177i or the location of the imaged ophthalmic structure and a reference of the imaging system. The generating the misalignment-reduction response 230 can include reducing the angular misalignment by adjusting the fixation light system 140 and reducing the lateral misalignment by operating the gantry controller 150. As the first phase of reducing the misalignment may only reduce the misalignment but not eliminate it, the reducing the angular misalignment and the reducing the lateral misalignment phases can be repeated iteratively and alternately in some implementations.

In some embodiments, the generating the misalignment-reduction response 230 can include using the locator light as a second fixation light 175. In these embodiments, the reducing the lateral and the angular misalignment can include instructing the patient 8 to align the first fixation light 145 and the locator/second fixation light 175.

Finally, some implementations of the ophthalmic imaging system may include an imaging device that generates an image of an imaged eye of the patient and a processor that determines a misalignment of the imaged eye and the imaging device by processing the generated image. The processor can control a fixation light system to project a fixation light on an eye of the patient to reduce an angular misalignment, and control a gantry to adjust a movable optical element of the system to reduce a lateral misalignment.

Some implementation of the ophthalmic imaging system can include an indicator light system that projects an indicator light on the imaged eye to provide misalignment information for the processor.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

The invention claimed is:

1. An ophthalmic system, comprising:
   an ophthalmic imaging device configured to generate an image of a portion of an imaged eye of a patient;
   an image processor, configured
     to determine a misalignment of the imaged eye and the imaging device by processing the generated image, and
     to generate a control signal according to the determined misalignment; and
   a misalignment-reduction system, configured
     to receive the control signal, and
     to generate a misalignment-reduction response.

2. The ophthalmic system of claim 1, the ophthalmic imaging device comprising:
   an electronic sensing system that senses a collected imaging light from the imaged eye, including at least one of
     a Charge-Coupled Device (CCD) array, a Complementary Metal-Oxide Semiconductor (CMOS) array, a pixel-array, and an electronic sensor array; and
   an electronic display system that displays the image of a portion of the imaged eye in relation to the sensed collected imaging light, including at least one of
     a Light Emitting Diode (LED) display, an organic LED (OLED) display, an active matrix OLED (AMOLED) display, an a plasma screen, an electronic display, a computer display, a Liquid Crystal Display (LCD) screen, a Cathode Ray Tube (CRT) display, a video-module, a video microscope display, a stereo video microscope display, a high definition (HD) video microscope, a processor-based image system, an opto-mechanical projector of the electronic or digital type, and a light-source movable by an electro-mechanical actuator.

3. The ophthalmic system of claim 1, wherein:
the image processor is configured
　to identify an ophthalmic structure in the image, and
　to determine a measure of misalignment by determining a location of the ophthalmic structure relative to a reference of the imaging device.

4. The ophthalmic system of claim 3, wherein:
the image processor is configured to identify the ophthalmic structure by determining a high-gradient line in the image, separating image elements with substantially different brightness or color.

5. The ophthalmic system of claim 4, wherein:
the image processor is configured
　to fit at least one of a circle and an ellipse to the high-gradient line by measuring radial distances between the high-gradient line and the circle or ellipse;
　to determine a location coordinate of the fitted circle or ellipse by minimizing a measure of the radial distances; and
　to determine a misalignment-measure by relating the determined location coordinate and a coordinate of the reference.

6. The ophthalmic system of claim 3, wherein:
the image processor is configured
　to determine a high-contrast line in the image;
　to determine misalignment distances between the high-contrast line and a targeting pattern; and
　to determine a misalignment-measure from the misalignment distances.

7. The ophthalmic system of claim 3, wherein:
the reference of the imaging device is at least one of
　an objective, a patient module, a docking tip, an interface, a contact lens, a pupil, a viewing frame, a reference frame, and an internal lens of the ophthalmic system; and
the imaging device is configured to generate a reference pattern related to the reference to assist the image processor to determine the misalignment of the imaged eye and the imaging device.

8. The ophthalmic system of claim 3, wherein:
the recognized ophthalmic structure is a limbus of the imaged eye.

9. The ophthalmic system of claim 1, wherein:
at least a portion of the image processed by the image processor is not displayed by the imaging device.

10. The ophthalmic system of claim 1, wherein:
the misalignment-reduction system comprises a fixation light source; and
the misalignment-reduction response comprises the fixation light source generating a fixation light in response to the received control signal.

11. The ophthalmic system of claim 10, wherein:
the fixation light source is configured
　to generate the fixation light for a non-imaged eye of the patient; and
　to move the generated fixation light according to the received control signal to assist a reduction of a misalignment between the imaged eye and a reference-component of the ophthalmic system.

12. The ophthalmic system of claim 10, the fixation light source comprising at least one of:
　a LED array, an organic LED (OLED) array, an active matrix OLED (AMOLED) array, a plasma screen, an electronic display, a computer display, an LCD screen, a video-module, an opto-mechanical projector, a CRT display, a slit-lamp, a processor-based image system, and a light-source movable by an electro-mechanical actuator.

13. The ophthalmic system of claim 10, wherein:
the fixation light source is configured to generate the fixation light to guide the patient to reduce an angular misalignment.

14. The ophthalmic system of claim 13, wherein:
the image processor is configured to determine the angular misalignment by
　fitting an ellipse to a high-contrast line of the image; and
　analyzing at least one of an aspect ratio and an area of the fitted ellipse.

15. The ophthalmic system of claim 10, wherein:
the fixation light source comprises a collimator to generate a fixation light to guide the patient to reduce a lateral misalignment.

16. The ophthalmic system of claim 1, wherein:
the misalignment-reduction system comprises
　a gantry, configured to move a movable portion of the imaging device; and
　a gantry controller, configured
　　to receive the control signal from the image processor, and
　　to move the gantry according to the received control signal; and
the misalignment-reduction response comprises the gantry controller moving the gantry and thus the movable portion of the imaging device to reduce a lateral misalignment.

17. The ophthalmic system of claim 16, wherein:
the gantry is also part of the ophthalmic imaging device.

18. The ophthalmic system of claim 1, wherein:
the misalignment-reduction system comprises
　a support-gantry, configured to move a patient support relative to the imaging device; and
　a gantry controller, configured
　　to receive the control signal from the image processor, and
　　to move the support-gantry according to the received control signal; and
the misalignment-reduction response comprises the gantry controller moving the support-gantry and thus the patient support to reduce a lateral misalignment.

19. The ophthalmic system of claim 1, wherein:
the image processor is configured to determine an angular and a lateral misalignment by processing the image; and
the misalignment-reduction system comprises only one of a fixation light source and a gantry controller.

20. The ophthalmic system of claim 1, wherein:
the image processor is configured to determine an angular and a lateral misalignment; and
the misalignment-reduction system comprises a fixation light source, a gantry and a gantry controller.

21. The ophthalmic system of claim 20, wherein:
the image processor is configured to determine an angular and a lateral misalignment by processing the image and a misalignment information.

22. The ophthalmic system of claim 21, wherein:
the imaging system comprises a locator light source, configured to project a locator light on the imaged eye; and
the image processor is configured
　to identify an apical reflected locator light in the image generated by the imaging device; and
　to determine the misalignment information by analyzing the apical reflected locator light.

23. The ophthalmic system of claim 22, wherein:
the misalignment information is at least one of
an angular misalignment information, related to a vector in the image between the apical reflected locator light and a location of an imaged ophthalmic structure; and
a lateral misalignment information, related to a vector in the image between a reference of the imaging system and at least one of the apical reflected locator light and the location of an imaged ophthalmic structure.

24. The ophthalmic system of claim 23, wherein:
the ophthalmic system is configured
to reduce the angular misalignment by adjusting the fixation light source; and
to reduce the lateral misalignment by operating the gantry controller.

25. The ophthalmic system of claim 22, wherein:
the fixation light is adjustable so that the locator light and a location of an imaged ophthalmic structure can be aligned by adjusting the fixation light.

26. The ophthalmic system of claim 22, wherein:
the fixation light source and the locator light source are capable of operating at different wavelengths.

27. The ophthalmic system of claim 26, wherein:
the locator light is invisible for the imaged eye.

28. The ophthalmic system of claim 1, comprising:
a patient interface, configured to dock to the imaged eye of the patient after the misalignment-reduction system executed the misalignment-reduction response.

29. The ophthalmic system of claim 1, wherein:
the misalignment-reduction system comprises a fixation light source, configured
to generate a fixation light for the imaged eye of the patient; and
to adjust the generated fixation light according to the received control signal to assist a reduction of a misalignment between the imaged eye and a reference-component of the ophthalmic system.

30. The ophthalmic system of claim 29, comprising:
a locator light, focusable to a second focal point different from a first focal point of the fixation light.

31. A method of aligning an eye with an ophthalmic system, the method comprising:
generating an image of a portion of an imaged eye of a patient by an ophthalmic imaging device;
determining a misalignment of the imaged eye and the imaging device by an image processor processing the generated image; and
generating a misalignment-reduction response electronically by a misalignment-reduction system based on the determined misalignment.

32. The method of claim 31, the determining the misalignment comprising:
identifying an ophthalmic structure in the image; and
determining a location of the ophthalmic structure relative to a reference of the imaging device.

33. The method of claim 31, the generating the misalignment-reduction response comprising:
generating a fixation light by a fixation light source according to the determined misalignment.

34. The method of claim 33, the generating the fixation light comprising:
generating the fixation light to guide the patient to reduce an angular misalignment.

35. The method of claim 33, the generating the fixation light comprising:
generating a fixation light to guide the patient to reduce a lateral misalignment, wherein
the fixation light source comprises a collimator.

36. The method of claim 33, wherein:
the generating the fixation light comprises
generating the fixation light for a non-imaged eye of the patient; and
the generating the misalignment-reduction response comprises
adjusting the fixation light according to the determined misalignment to assist the patient to reduce the misalignment.

37. The method of claim 33, wherein:
the generating the fixation light comprises
generating the fixation light for the imaged eye of the patient; and
the generating the misalignment-reduction response comprises
adjusting the fixation light according to the determined misalignment to assist the patient to reduce the misalignment.

38. The method of claim 31, the generating the misalignment-reduction response comprising:
moving a gantry of the imaging system by a gantry controller to reduce a lateral misalignment.

39. The method of claim 31, wherein:
the determining the misalignment comprises
determining an angular and a lateral misalignment by the image processor processing the image and a misalignment information; and
the generating the misalignment-reduction response comprises
adjusting a fixation light of a fixation light system and a gantry controller.

40. The method of claim 39, the determining the misalignment comprising:
projecting a locator light onto the imaged eye by a locator light system;
locating an apical reflected locator light in the image generated by the imaging device; and
determining the misalignment information using the located apical reflected locator light.

41. The method of claim 40, the determining the misalignment information comprising:
determining an angular misalignment information, related to a vector in the image between the apical reflected locator light and a location of an imaged ophthalmic structure; and
determining a lateral misalignment information, related to a vector in the image between a reference of the imaging system and at least one of the apical reflected locator light and the imaged ophthalmic structure.

42. The method of claim 41, the generating the misalignment-reduction response comprising:
reducing the angular misalignment by adjusting the fixation light; and
reducing the lateral misalignment by operating the gantry controller.

43. The method of claim 42, wherein:
the reducing the angular misalignment and the reducing the lateral misalignment are repeated iteratively.

44. The method of claim 40, the generating the misalignment-reduction response comprising:
projecting the fixation light into the imaged eye; and
reducing the lateral and the angular misalignment by causing the head of the patient to move laterally to align the locator light and the fixation light.

45. An ophthalmic system, comprising:

an imaging device that generates an image of an imaged eye of a patient;

an image processor that determines an angular and a lateral misalignment of the imaged eye and the imaging device by processing the generated image;

a fixation light system that projects a fixation light on an eye of the patient to assist a reduction of the angular misalignment; and a gantry that adjusts a movable optic of the system to reduce the lateral misalignment.

46. The ophthalmic system of claim 45, comprising:

an indicator light system that projects an indicator light on the imaged eye to provide a misalignment information for the image processor.

* * * * *